(12) United States Patent
Rawson

(10) Patent No.: US 7,659,305 B2
(45) Date of Patent: Feb. 9, 2010

(54) THERAPEUTIC PROLINE DERIVATIVES

(75) Inventor: David James Rawson, Kent (GB)

(73) Assignee: Pfizer Inc., New York, NY (US)

( * ) Notice: Subject to any disclaimer, the term of this patent is extended or adjusted under 35 U.S.C. 154(b) by 979 days.

(21) Appl. No.: 10/698,354

(22) Filed: Oct. 30, 2003

(65) Prior Publication Data

US 2004/0132801 A1 Jul. 8, 2004

Related U.S. Application Data

(60) Provisional application No. 60/428,630, filed on Nov. 22, 2002.

(30) Foreign Application Priority Data

Oct. 31, 2002 (GB) .................................. 0225379.7

(51) Int. Cl.
*A61K 31/40* (2006.01)
*A01N 43/36* (2006.01)
(52) U.S. Cl. ..................................................... 514/423
(58) Field of Classification Search .................. None
See application file for complete search history.

(56) References Cited

U.S. PATENT DOCUMENTS

| | | | |
|---|---|---|---|
| 4,024,175 | A | 5/1977 | Satzinger et al. |
| 4,087,544 | A | 5/1978 | Satzinger et al. |
| 4,311,705 | A | 1/1982 | Ondetti et al. |
| 4,316,905 | A | 2/1982 | Krapcho |
| 4,316,906 | A | 2/1982 | Ondetti et al. |
| 4,462,943 | A | 7/1984 | Petrillo, Jr. et al. |
| 5,385,889 | A * | 1/1995 | Kyle et al. ................ 514/15 |

FOREIGN PATENT DOCUMENTS

| | | |
|---|---|---|
| EP | 0499873 | 2/1992 |
| EP | 0979817 | 3/1998 |
| EP | 1129706 | 9/2001 |
| EP | 0574174 | 8/2003 |
| GB | 2028327 | 3/1980 |
| GB | 2078733 | 1/1982 |
| GB | 2205832 | 12/1998 |
| JP | 04154731 A | 5/1992 |
| WO | WO 95/13069 | 5/1995 |
| WO | WO9513069 | 5/1995 |
| WO | WO9961424 | 4/1999 |
| WO | WO01/19817 | 3/2001 |
| WO | WO0162728 | 8/2001 |
| WO | WO 0162757 | 8/2001 |
| WO | WO02/22568 | 3/2002 |
| WO | WO02/30871 | 4/2002 |
| WO | WO02/22575 | 3/2003 |

OTHER PUBLICATIONS

IUPAC Compendium of Chemical Terminology. "Cis-Trans Isomers". [Online] 1997 [Retrieved on Sep. 6, 2007]. Retrieved from the Internet: <URL: http://www.iupac.org/goldbook/C01093.pdf>.*

Julien RM. "Chapter 2: Pharmacodynamics: How Drugs Act". A Primer of Drug Action (Ninth Edition). Worth Publishers, 2001:37-57.*

Misra R, "Interphenylene 7-Oxabicyclo[2.2.1]heptane Oxazoles. Highly Potent, Selective and Long-Acting Thromboxane A2 Receptor Antagonists" J. Med. Chem 1998, pp. 1401-1417, vol. 36.

Papaioannou D, "Simple Synthesis of cis-4-Hydroxy-L-Proline and Derivatives Suitable for Use as Intermediates in Peptide Synthesis" Acta Chem Scand 1990, pp. 243-251 vol. 44.

Murakami, Y, Stereochemical Studies. XIII.1) Determination of the Absolute configuration of Mecraptosuccinic Acid by Chemical Correlation with Glyceraldehyde2) Chem. Pharm. Bull, 1972 pp. 543-549 vol. 20.

Eswarakrishnan, V. "Sulfinic Acids and Related Compounds. 13. Unsymmetrical Disulfides Based on Methyl 4-Mercaptobutanesulfinate adn 4(S)- or 4(R)-Mecraptorprolines" J. Org. Chem 1981 pp. 4182-4187 vol. 46.

Ezquerra J, "Synthesis of Enantiomerically Pure 4-Substituted Glutamic Acids and Prolines; General Aldol Reaction of Pyroglutamate Lactam Lithium Enolate Mediated by Et20-BF3" J. Org. Chem., 1995, pp. 2925-2930, vol. 60.

Gee, N "The Novel Anticonvulsant Drug, Gabapentin (Neurontin), Binds to the alpha2beta Subunit of a Calcium Channel" J. Biol Chem. 1996, pp. 5768-5776, vol. 271(10).

Gong H, "Tissue-specific Expression and Gabapentin-Binding Properties of Calcium Channel alpha 2 beta Subunit Subtypes" J Membrane Biol, 2001 pp. 35-43 vol. 184.

Krapch J, "ANgiotensin-Converting Enzyme Inhibitors, Mercaptan, Carboxyalky Dipeptide, and Phosphinic Acid Inhibitors Incorporating 4-Substituted Prolines" J. Med. Chem, 1998 pp. 1148-1160 vol. 31.

(Continued)

*Primary Examiner*—Ardin Marschel
*Assistant Examiner*—Leslie A Royds
(74) *Attorney, Agent, or Firm*—Gregg C. Benson; A. Dean Olson

(57) ABSTRACT

The compounds of formula (I) or a pharmaceutically acceptable salt, solvate or pro-drug thereof, are proline derivatives useful in the treatment of epilepsy, faintness attacks, hypokinesia, cranial disorders, neurodegenerative disorders, depression, anxiety, panic, pain, fibromyalgia, arthritis, neuropathalogical disorders, sleep disorders, visceral pain disorders and gastrointestinal disorders. Processes for the preparation of the final products and intermediates useful in the process are included. Pharmaceutical compositions containing one or more of the compounds are also included.

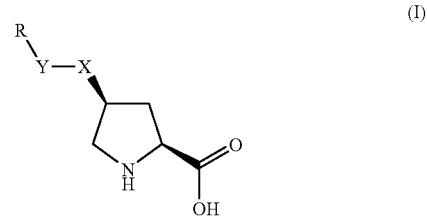

(I)

9 Claims, No Drawings

OTHER PUBLICATIONS

Marais E, "Calcium Channel alpha2beta Subunites-Structure and Gabapentin Binding" Molecular Pharm, 2001 pp. 1243-1248, vol. 59.

Plucinska K, "Multiple Binding Modes for the Receptor-Bound Conformations of Cyclic AII Agonists" J. Med. Chem., 1993, pp. 1902-1913, vol. 36.

Qin N, "Molecular Cloning and Characterization of the Human Voltage-Gated Calsium Channel alpha 2 beta-4 Subunit" Molecular Pharm 2002 pp. 485-496, vol. 62.

Verbiscar A, "Synthesis of cis-and trans- 4-Mercapto-L-proline Derivatives" J. Org. Chem., 1970 pp. 1924-1927, vol. 35 No. 6.

Ezquerra, J., et al., *J. Org. Chem.*, vol. 60, pp. 2925-2930 (1995).

* cited by examiner

THERAPEUTIC PROLINE DERIVATIVES

This United States Utility Application claims the benefit of United Kingdom Application Number 0225379.7 filed Oct. 31, 2002 and U.S. Provisional Application No. 60/428,630 filed Nov. 22, 2002.

FIELD OF THE INVENTION

This invention relates to proline derivatives useful as pharmaceutical agents, to processes for their production, to pharmaceutical compositions containing them, and to their use for the treatment of the conditions set out below.

BACKGROUND TO THE INVENTION

Gabapentin (Neurontin®) is an anti-convulsant agent that is useful in the treatment of epilepsy and has recently been shown to be a potential treatment for neurogenic pain. It is 1-(aminomethyl)-cyclohexylacetic acid of structural formula:

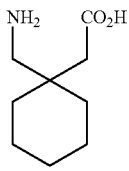

Gabapentin is one of a series of compounds of formula

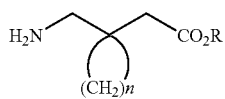

in which R is hydrogen or a lower alkyl radical and n is 4, 5, or 6. These compounds are described U.S. Pat. No. 4,024,175 and its divisional U.S. Pat. No. 4,087,544. Gabapentin is useful in the treatment of a number of diseases, including pain and epilepsy.

Gabapentin and related compounds, such as pregabalin, may be referred to as alpha-2-delta ligands. An alpha-2-delta receptor ligand is any molecule which binds to any sub-type of the human calcium channel alpha-2-delta subunit. The calcium channel alpha-2-delta subunit comprises a number of sub-types which have been described in the literature:

e.g. N. S. Gee, J. P. Brown, V. U. Dissanayake, J. Offord, R. Thurlow, and G. N. Woodruff, *J-Biol-Chem* 271 (10):5768-76, 1996, (type 1);
Gong, J. Hang, W. Kohler, Z. Li, and T-Z. Su, *J. Membr. Biol.* 184 (1):35-43, 2001, (types 2 and 3);
E. Marais, N. Klugbauer, and F. Hofmann, *Mol. Pharmacol.* 59 (5):1243-1248, 2001. (types 2 and 3); and
N. Qin, S. Yagel, M. L. Momplaisir, E. E. Codd, and M. R. D'Andrea. *Mol. Pharmacol.* 62 (3):485-496, 2002, (type 4). They may also be known as GABA analogs.

International Patent Applications Nos. WO0230871 and WO0222568 describe compounds of the type I and type II, respectively,

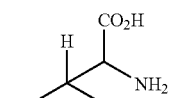

I

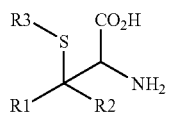

II which also have affinity for the gabapentin binding site and have physiological activities similar to gabapentin, particularly with respect to analgesia.

International Patent Application No. WO0119817 describes 3-pyrrolidinyloxy-3'-pyridyl ether compounds which are useful for controlling neurotransmitter release.

International Patent Application No. WO0222575 describes benzamidine derivatives which are serine protease inhibitors.

Certain of the compounds embraced within the broadest formula of the present invention have been disclosed for utilities not connected with the present invention, in particular according to Table 1:

TABLE 1

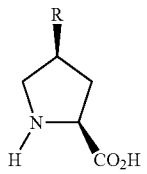

| R | Ref |
|---|---|
| BnO— (2S,4S)-4-(benzyloxy)pyrrolidine-2-carboxylic acid | Acta Chem Scand, 1990, 243-51 |
| BnS— (2S,4S)-4-(benzylthio)pyrrolidine-2-carboxylic acid | Chem Pharm Bull, 1972, 543-49<br>J Med Chem, 1993, 1902-13<br>JOC, 1981, 4182-4187 |

TABLE 1-continued

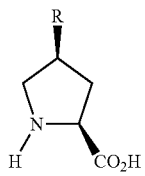

| R | Ref |
|---|---|
| 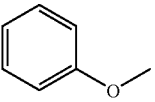<br>(2S,4S)-4-phenoxypyrrolidine-2-carboxylic acid | J. Med Chem, 1988, 1148-60 |
| 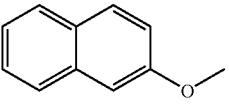<br>(2S,4S)-4-(2-naphthyloxy)pyrrolidine-2-carboxylic acid | J Med Chem, 1988, 1148-60 |
| 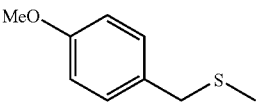<br>(2S,4S)-4-[(4-methoxybenzyl)thio]pyrrolidine-2-carboxylic acid | JOC, 1970, 1924-1927<br>J Med Chem, 1993, 1902-1912 |
| 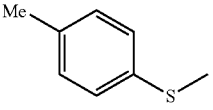<br>(2S,4S)-4-[(4-methylphenyl)thio]pyrrolidine-2-carboxylic acid | J Med Chem, 1993, 1402-13 |
| 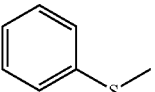<br>(2S,4S)-4-(phenylthio)pyrrolidine-2-carboxylic acid | J Med Chem, 1988, 1148-60 |
| 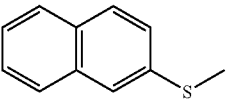<br>(2S,4S)-4-(2-naphthylthio)pyrrolidine-2-carboxylic acid | J Med Chem, 1988, 1148-60 |
| Bn—<br>(2S,4S)-4-benzylpyrrolidine-2-carboxylic acid | J Med Chem, 1988, 1148-60<br>JOC, 1995, 2925-30 |
| 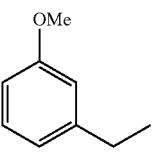<br>(2S,4S)-4-(3-methoxybenzyl)pyrrolidine-2-carboxylic acid | JOC, 1995, 2925-30 |

TABLE 1-continued

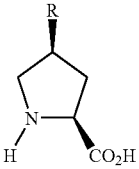

| R | Ref |
|---|---|
| 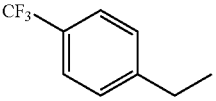<br>(2S,4S)-4-[4-(trifluoromethyl)benzyl]pyrrolidine-2-carboxylic acid | JOC, 1995, 2925-30 |
| 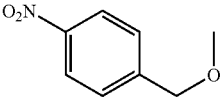<br>(2S,4S)-4-[(4-nitrobenzyl)oxy]pyrrolidine-2-carboxylic acid | Japanese Patent Application No. JP 04154731 |
| 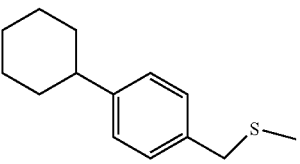<br>(2S,4S)-4-[(4-cyclohexylbenzyl)thio]pyrrolidine-2-carboxylic acid | Japanese Patent Application No. JP 10265456 |
| 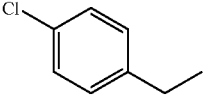<br>(2S,4S)-4-(4-chlorobenzyl)pyrrolidine-2-carboxylic acid | UK Patent Application No. GB 2078733 |
| 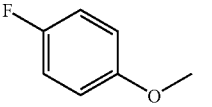<br>(2S,4S)-4-(4-fluorophenoxy)pyrrolidine-2-carboxylic acid | U.S. Pat. No. 4,316,906 |
| 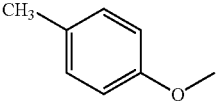<br>(2S,4S)-4-(4-methylphenoxy)pyrrolidine-2-carboxylic acid | U.S. Pat. No. 4,316,906 |
| 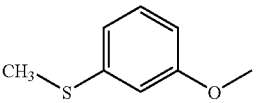<br>(2S,4S)-4-(3-methylthiophenoxy)pyrrolidine-2-carboxylic acid | U.S. Pat. No. 4,316,906 |
| 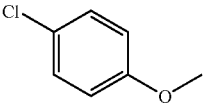<br>(2S,4S)-4-(4-chlorophenoxy)pyrrolidine-2-carboxylic acid | U.S. Pat. No. 4,316,906 |

TABLE 1-continued

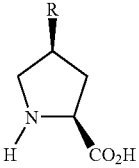

| R | Ref |
|---|---|
| 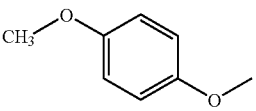<br>(2S,4S)-4-(4-methoxyphenoxy)pyrrolidine-2-carboxylic acid | U.S. Pat. No. 4,316,906 |
| 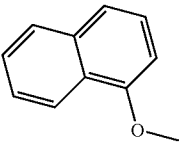<br>(2S,4S)-4-(1-naphthalenyloxy)pyrrolidine-2-carboxylic acid | U.S. Pat. No. 4,316,906 |
| 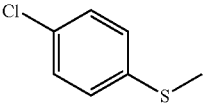<br>(2S,4S)-4-(4-chlorophenylthio)pyrrolidine-2-carboxylic acid | U.S. Pat. No. 4,316,906 |
| 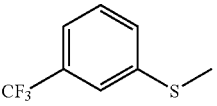<br>(2S,4S)-4-(3-trifluoromethylphenylthio)pyrrolidine-2-carboxylic acid | U.S. Pat. No. 4,316,906 |
| 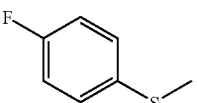<br>(2S,4S)-4-(4-fluorophenylthio)pyrrolidine-2-carboxylic acid | UK Patent Application No. GB 2028327 |
| 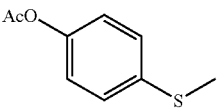<br>(2S,4S)-4-(4-acetyloxyphenylthio)pyrrolidine-2-carboxylic acid | UK Patent Application No. GB 2028327 |
| 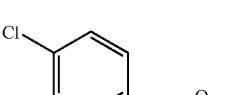<br>(2S,4S)-4-(4-chlorobenzyloxy)pyrrolidine-2-carboxylic acid | U.S. Pat. No. 4,311,705 |

TABLE 1-continued

| R | Ref |
|---|---|
| (2S,4S)-4-(4-phenyl-phenoxy)pyrrolidine-2-carboxylic acid | U.S. Pat. No. 4,311,705 |
| (2S,4S)-4-(4-phenyl-phenylthio)pyrrolidine-2-carboxylic acid | U.S. Pat. No. 4,311,705 |
| (2S,4S)-4-(4-methyl-benzyloxy)pyrrolidine-2-carboxylic acid | U.S. Pat. No. 4,462,943 |
| (2S,4S)-4-(4-fluorobenzyl)pyrrolidine-2-carboxylic acid | U.S. Pat. No. 4,462,943 |

SUMMARY OF THE INVENTION

The present invention provides proline derivatives and their pharmaceutically acceptable salts, solvates, polymorphs and pro-drugs, useful in the treatment of a variety of disorders including epilepsy, faintness attacks, hypokinesia, cranial disorders, neurodegenerative disorders, depression, anxiety, panic, pain, fibromyalgia, sleep disorders, osteoarthritis, rheumatoid arthritis, and neuropathalogical disorders. The compounds provided may also be useful in the treatment of visceral pain, functional bowel disorders such as gastro-esophageal reflux, dyspepsia, irritable bowel syndrome and functional abdominal pain syndrome, and inflammatory bowel diseases such as Crohn's disease, ileitis, and ulcerative colitis, and other types of visceral pain associated with dysmenorrhea, pelvic pain, cystitis and pancreatitis. They may also be used for the treatment of premenstrual syndrome.

Thus, the present invention provides use of a compound of formula (I):

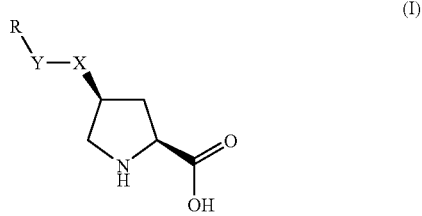

wherein
either X is O, S, NH or $CH_2$ and Y is $CH_2$ or a direct bond, or Y is O, S or NH and X is $CH_2$; and
R is a 3-12 membered cycloalkyl, 4-12 membered heteroalkyl, aryl or heteroaryl, where any ring may be optionally substituted with one or more substituents independently selected from halogen, hydroxy, cyano, nitro, amino, hydroxycarbonyl, $C_1$-$C_6$ alkyl, $C_1$-$C_6$ alkenyl, $C_1$-$C_6$ alkynyl, $C_1$-$C_6$ alkoxy, hydroxy$C_1$-$C_6$ alkyl, $C_1$-$C_6$ alkoxy$C_1$-$C_6$ alkyl, perfluoro $C_1$-$C_6$ alkyl, perfluoro$C_1$-$C_6$ alkoxy, $C_1$-$C_6$ alkylamino, di-$C_1$-$C_6$ alkylamino, amino$C_1$-$C_6$ alkyl, $C_1$-$C_6$ alkylamino$C_1$-$C_6$ alkyl, di-$C_1$-$C_6$ alkylamino$C_1$-$C_6$ alkyl, $C_1$-$C_6$acyl, $C_1$-$C_6$acyloxy, $C_1$-$C_6$acyloxy$C_1$-$C_6$alkyl, $C_1$-$C_6$acylamino,
$C_1$-$C_6$ alkylthio, $C_1$-$C_6$ alkylthiocarbonyl, $C_1$-$C_6$ alkylthioxo, $C_1$-$C_6$ alkoxycarbonyl, $C_1$-$C_6$ alkylsulfonyl, $C_1$-$C_6$ alkylsulfonylamino, aminosulfonyl, $C_1$-$C_6$ alkylaminosulfonyl, di-$C_1$-$C_6$ alkylaminosulfonyl, 3-8 membered cycloalkyl, 4-8 membered heterocycloalkyl, phenyl and monocyclic heteroaryl;

or a pharmaceutically acceptable salt, solvate or pro-drug thereof, in medical therapy.

As a further aspect, the present invention provides the use of a compound of formula (I) or a pharmaceutically acceptable salt, solvate or pro-drug thereof, in the manufacture of a medicament for the treatment of a disorder for which the alpha-2-delta receptor is implicated. suitably, a disorder for which the alpha-2-delta receptor is implicated is selected from epilepsy, faintness attacks, hypokinesia, cranial disorders, neurodegenerative disorders, depression, anxiety, panic, pain, fibromyalgia, irritable bowel syndrome, sleep disorders, osteoarthritis, rheumatoid arthritis, neuropathological disorders, visceral pain, functional bowel disorders, inflammatory bowel diseases, pain associated with dysmenorrhea, pelvic pain, cystitis and pancreatitis.

As an alternative of the first further aspect of the present invention, there is provided a method of treatment of a mammal, including human, of a disorder for which the alpha-2-delta receptor is implicated, comprising effective administration of a compound of formula (I), or a pharmaceutically acceptable salt, solvate or pro-drug thereof.

According to formula (I), suitably X is O, S, NH or $CH_2$ and Y is $CH_2$ or a direct bond, or X is $CH_2$ and Y is O. Preferably, —Y—X— is a methylene, methyleneoxy, methylenethio, oxymethylene, amino, thio or oxy link. Particularly preferred, —Y—X— is an oxy, methylene or oxymethylene link.

According to formula (I), R is suitably heteroaryl, aryl, 4-8 membered heterocycloalkyl or 3-12 membered cycloalkyl, optionally substituted with one or more substituents independently selected from halogen, $C_1$-$C_6$ alkyl, $C_1$-$C_6$ alkoxy, $C_1$-$C_6$ alkoxy $C_1$-$C_6$ alkyl, perfluoro $C_1$-$C_6$ alkyl, perfluoro $C_1$-$C_6$ alkoxy, cyano, amino $C_1$-$C_6$ alkyl, di-$C_1$-$C_6$ alkylamino$C_1$-$C_6$ alkyl and monocyclic heteroaryl. R is more suitably optionally substituted aryl, 4-8 membered heterocycloalkyl or 3-12 membered cycloalkyl. R is preferably optionally substituted phenyl, cyclohexyl, dihydro-benzofuranyl or isoquinolyl. R is more preferably optionally substituted phenyl. Most preferably, R is phenyl, substituted in the meta-position and optionally di-substituted.

According to formula (I), suitable optional substituents on R, preferably at least in the meta position, are independently selected from hydroxy, ($C_1$-$C_6$)alkoxy or halogen, preferably methoxy, fluoro, chloro or bromo, most preferably fluoro or chloro.

Particularly preferred compounds of the invention include those in which each variable in Formula (I) is selected from the suitable groups for each variable. Even more preferable compounds of the invention include those where each variable in Formula (I) is selected from the preferred or more preferred groups for each variable.

It will be understood that certain compounds described by formula (I), including those specifically described herein, are novel and, therefore, individually and collectively constitute a further aspect of the present invention.

Preferred compounds of formula (I) are selected from:
(2S,4S)-4-(Benzylsulfanyl)-pyrrolidine-2-carboxylic acid;
(2S,4S)-4-[(4-cholorobenzyl)oxy]-pyrrolidine-2-carboxylic acid;
(2S,4S)-4-[(4-bromophenylthio]-pyrrolidine-2-carboxylic acid;
(2S,4S)-4-phenylthio-pyrrolidine-2-carboxylic acid;
(2S,4S)-4-[2-flourophenoxy]-pyrrolidine-2-carboxylic acid;
(2S,4S)-4-[(4-chlorophenoxy]-pyrrolidine-2-carboxylic acid;
(2S,4S)-4-}2-isoquinolinoxy}-pyrrolidine-2-carboxylic acid;
(2S,4S)-4-(3-Chloro-phenoxy)-pyrrolidine-2-carboxylic acid;
(2S,4S)-4-(Benzyloxy)-pyrrolidine-2-carboxylic acid; and
(2S,4S)-4-(3-Fluoro-benzyl)-pyrrolidine-2-carboxylic acid.
(2S,4S)-4-(2,3-Difluoro-benzyl)-pyrrolidine-2-carboxylic acid;
(2S,4S)-4-(2,5-Difluoro-benzyl)-pyrrolidine-2-carboxylic acid;
(2S,4S)-4-Cyclohexylmethyl-pyrrolidine-2-carboxylic acid;
(2S,4S)-4-(3-Methoxy-benzyl)-pyrrolidine-2-carboxylic acid;
(2S,4S)-4-(3-Fluoro-phenoxymethyl-pyrrolidine-2-carboxylic acid;
(2S,4S)-4-(3-Chloro-phenoxymethyl)-pyrrolidine-2-carboxylic acid;
(2S,4S)-4-(2,3-Dihydro-benzofuran-6-yloxy)-pyrrolidine-2-carboxylic acid;
(2S,4S)-4-(3-Chloro-phenylamino)-pyrrolidine-2-carboxylic acid;
(2S,4S)-4-(2,5-Difluoro-phenoxymethyl)-pyrrolidine-2-carboxylic acid;
(2S,4S)-4-(2,3-Difluoro-phenoxymethyl)-pyrrolidine-2-carboxylic acid; and
(2S,4S)-4-(3-Methoxy-phenoxymethyl)-pyrrolidine-2-carboxylic acid.
(2S,4S)-4-(2,3-Difluoro-phenoxymethyl)-pyrrolidine-2-carboxylic acid; and
(2S,4S)-4-(3-Methoxy-phenoxymethyl)-pyrrolidine-2-carboxylic acid.

Even more preferred compounds of formula (I) are selected from
(2S,4S)-4-(3-Chloro-phenoxy)-pyrrolidine-2-carboxylic acid;
(2S,4S)-4-(3-Fluoro-benzyl)-pyrrolidine-2-carboxylic acid;
(2S,4S)-4-(2,3-Difluoro-benzyl)-pyrrolidine-2-carboxylic acid;
(2S,4S)-4-(2,5-Difluoro-benzyl)-pyrrolidine-2-carboxylic acid;
(2S,4S)-4-Cyclohexylmethyl-pyrrolidine-2-carboxylic acid;
(2S,4S)-4-(3-Methoxy-benzyl)-pyrrolidine-2-carboxylic acid;
(2S,4S)-4-(3-Fluoro-phenoxymethyl)-pyrrolidine-2-carboxylic acid;
(2S,4S)-4-(2,5-Difluoro-phenoxymethyl)-pyrrolidine-2-carboxylic acid;
(2S,4S)-4-(2,3-Difluoro-phenoxymethyl)-pyrrolidine-2-carboxylic acid; and
(2S,4S)-4-(3-Methoxy-phenoxymethyl)-pyrrolidine-2-carboxylic acid.

Certain compounds within the scope of formula (I) have been disclosed for non-therapeutic use. Thus, as a further aspect, there is provided a compound of formula (I) or a pharmaceutically acceptable salt, solvate, polymorph or pro-drug thereof, excluding any compound previously disclosed in the art for a non-therapeutic use, particularly those described in Table 1 above, i.e. (2S,4S)-4-(benzyloxy)pyrrolidine-2-carboxylic acid, (2S,4S)-4-(benzylthio)pyrrolidine-2-carboxylic acid, (2S,4S)-4-phenoxypyrrolidine-2-carboxylic acid, (2S,4S)-4-(2-naphthyloxy)pyrrolidine-2-carboxylic acid, (2S,4S)-4-[(4-methoxybenzyl)thio]pyrrolidine-2-carboxylic acid, (2S,4S)-4-[(4-methylphenyl)

thio]pyrrolidine-2-carboxylic acid, (2S,4S)-4-(phenylthio)pyrrolidine-2-carboxylic acid, (2S,4S)-4-(2-naphthylthio)pyrrolidine-2-carboxylic acid, (2S,4S)-4-benzylpyrrolidine-2-carboxylic acid, (2S,4S)-4-(3-methoxybenzyl)pyrrolidine-2-carboxylic acid, (2S,4S)-4-[4-(trifluoromethyl)benzyl]pyrrolidine-2-carboxylic acid, (2S,4S)-4-[(4-nitrobenzyl)oxy]pyrrolidine-2-carboxylic acid, (2S,4S)-4-[(4-cyclohexylbenzyl)thio]pyrrolidine-2-carboxylic acid, (2S,4S)-4-(4-chlorobenzyl)pyrrolidine-2-carboxylic acid, (2S,4S)-4-(4-fluorophenoxy)pyrrolidine-2-carboxylic acid, (2S,4S)-4-(4-methylphenoxy)pyrrolidine-2-carboxylic acid, (2S,4S)-4-(3-methylthiophenoxy)pyrrolidine-2-carboxylic acid, (2S,4S)-4-(4-chlorophenoxy)pyrrolidine-2-carboxylic acid, (2S,4S)-4-(4-methoxyphenoxy)pyrrolidine-2-carboxylic acid, (2S,4S)-4-(1-naphthalenyloxy)pyrrolidine-2-carboxylic acid, (2S,4S)-4-(4-chlorophenylthio)pyrrolidine-2-carboxylic acid, trifluoromethylphenylthio)pyrrolidine-2-carboxylic acid, (2S,4S)-4-(4-fluorophenylthio)pyrrolidine-2-carboxylic acid, (2S,4S)-4-(4-acetyloxyphenylthio)pyrrolidine-2-carboxylic acid, (2S,4S)-4-(4-chlorobenzyloxy)pyrrolidine-2-carboxylic acid, (2S,4S)-4-(4-phenyl-phenoxy)pyrrolidine-2-carboxylic acid, (2S,4S)-4-(4-phenyl-phenylthio)pyrrolidine-2-carboxylic acid, (2S,4S)-4-(4-methylbenzyloxy)pyrrolidine-2-carboxylic acid and (2S,4S)-4-(4-fluorobenzyl)pyrrolidine-2-carboxylic acid.

As an alternative aspect of the present invention, there is provided a compound of formula (Ia), (Ib) or (Ic):

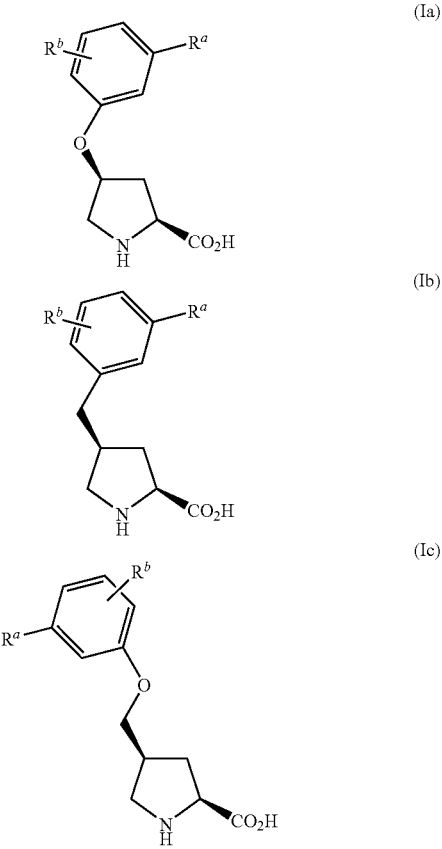

wherein $R^a$ and $R^b$ are independently selected from hydrogen, halogen, hydroxy, $(C_1-C_6)$alkoxy cyano, nitro, amino, hydroxycarbonyl, $C_1-C_6$ alkyl, $C_1-C_6$ alkenyl, $C_1-C_6$ alkynyl, $C_1-C_6$ alkoxy, hydroxy$C_1-C_6$ alkyl, $C_1-C_6$ alkoxy$C_1-C_6$ alkyl, perfluoro $C_1-C_6$alkyl, perfluoro$C_1-C_6$ alkoxy, $C_1-C_6$ alkylamino, di-$C_1-C_6$ alkylamino, amino$C_{1-C6}$ alkyl, $C_1-C_6$ alkylamino$C_{1-C6}$ alkyl di-$C_{1-C6}$ alkylamino$C_1-C_6$ alkyl, $C_1-C_6$acyl, $C_1-C_6$acyloxy, $C_1-C_6$acyloxy$C_1-C_6$ alkyl, $C_1-C_6$ acylamino, $C_1-C_6$ alkylthio, $C_1-C_6$ alkylthiocarbonyl, $C_1-C_6$ alkylthioxo, $C_1-C_6$ alkoxycarbonyl, $C_1-C_6$ alkylsulfonyl, $C_1-C_6$ alkylsulfonylamino, aminosulfonyl, $C_1-C_6$ alkylaminosulfonyl, di-$C_1-C_6$ alkylaminosulfonyl, 3-8 membered cycloalkyl, 4-8 membered heterocycloalkyl, phenyl and monocyclic heteroaryl; or a pharmaceutically acceptable salt, solvate or pro-drug thereof.

with the proviso that, for a compound of formulae (Ia) and (Ib), $R^a$ and $R^b$ cannot both be hydrogen and when $R^b$ is a para sustituent, $R^a$ cannot be hydrogen, for a compound of formulae (Ia), when $R^a$ is methylthio, $R^b$ cannot be hydrogen, and for a compound of formula (Ib), when $R^a$ is methoxy, $R^b$ cannot be hydrogen.

With reference to formula (Ia), (Ib) or (Ic), $R^a$ is suitably not hydrogen.

In the above definitions, halo means fluoro, chloro, bromo or iodo. Alkyl and alkoxy groups, containing the requisite number of carbon atoms, except where indicated, can be unbranched- or branched-chain. Examples of alkyl include straight and branched chain groups such as methyl, ethyl, n-propyl, i-propyl, n-butyl, i-butyl, sec-butyl and t-butyl. Examples of alkoxy include straight and branched chain groups such as methoxy, ethoxy, n-propoxy, i-propoxy, n-butoxy, i-butoxy, sec-butoxy and t-butoxy. Alkenyl and alkynyl groups as referred to herein include straight and branched ring aliphatic groups having one double or triple bond, respectively. Examples of alkenyl and alkynyl groups include ethenyl, prop-1-enyl, prop-2-enyl and ethynyl, prop-1-ynyl and prop-2-ynyl respectively.

4-8 membered heterocycloalkyl when used herein refers to a single saturated or partially unsaturated ring system containing at least one ring heteroatom independently selected from O, S and N. 4-12 membered heterocycloalkyl when used herein refers to a single saturated or partially unsaturated ring or fused ring system containing at least one ring heteroatom independently selected from O, S and N. Thus a polycyclic fused ring system containing one or more carbocyclic fused saturated, partially unsaturated or aromatic rings is within the definition of 4-12 membered heterocycloalkyl so long as the system also contains at least one fused ring which contains at least one of the aforementioned heteroatoms. Suitable heterocycloalkyl groups include pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, 2,3-dihydrobenzofuranyl etc.

Heteroaryl when used herein refers to a single aromatic ring or fused, suitably bicyclic, aromatic ring system containing at least one ring heteroatom independently selected from O, S and N. Thus a polycyclic fused ring system containing one or more carbocyclic fused saturated, partially unsaturated or aromatic rings is within the definition of heteroaryl so long as the system also contains at least one fused aromatic ring which contains at least one of the aforementioned heteroatoms. Suitable heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, etc.

$C_3$-$C_8$ cycloalkyl as used herein refers to a single saturated or partially unsaturated carbocyclic ring system. $C_3$-$C_{12}$ cycloalkyl as used herein refers to a single or fused carbocyclic ring system containing at least one saturated or partially unsaturated ring, where the other ring in a fused system may be phenyl. Suitable cycloalkyl groups include cyclopropyl, cyclobutyl, cyclopentyl, cyclohexyl, cycloheptyl, indane and 1,2,3,4-tetrahydronaphthylene groups.

Aryl when used herein refers to phenyl or naphthyl.

Acyl as used herein refers to aliphatic or cyclic hydrocarbons attached to a carbonyl group through which the substituent bonds.

DETAILED DESCRIPTION OF THE INVENTION

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Although the stereochemistry on the pyrrolidine ring of formula (I) is fixed, certain of the compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention also includes all suitable isotopic variations of a compound of the invention or a pharmaceutically acceptable salt thereof. An isotopic variation of a compound of the invention, or a pharmaceutically acceptable salt thereof, is defined as one in which at least one atom is replaced by an atom having the same atomic number but an atomic mass different from the atomic mass usually found in nature.

Examples of isotopes suitable for inclusion into compounds of the invention, and pharmaceutically acceptable salts thereof, include isotopes of hydrogen, carbon, nitrogen, oxygen, phosphorous, sulfur, fluorine and chlorine, such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively.

Certain isotopically-labelled compounds of formula (I) and pharmaceutically acceptable salts thereof, for example, those in which a radioactive isotope such as $^3$H or $^{14}$C is incorporated, are useful in drug and/or substrate tissue distribution studies. The radioactive isotopes tritium, i.e., $^3$H, and carbon-14, i.e., $^{14}$C, isotopes are particularly preferred in view of their ease of preparation and ready means of detection.

Substitution with heavier isotopes such as deuterium, i.e., $^2$H, may afford certain therapeutic advantages resulting from greater metabolic stability, for example, increased in vivo half-life or reduced dosage requirements and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of the present invention are amino acids. Since amino acids are amphoteric, pharmacologically compatible salts can be salts of appropriate non-toxic inorganic or organic acids or bases. Suitable acid addition salts are the hydrochloride/chloride, hydrobromide/bromide, hydroiodide/iodide, sulphate, bisulphate, nitrate, phosphate, hydrogen phosphate, acetate, fumarate, aspartate, besylate, bicarbonate/carbonate, camsylate, D and L-lactate, D and L-tartrate, edisylate, mesylate, malonate, orotate, gluceptate, methylsulphate, stearate, glucuronate, 2-napsylate, tosylate, hibenzate, nicotinate, isethionate, malate, maleate, citrate, gluconate, succinate, saccharate, benzoate, esylate, trifluoroacetate and pamoate salts.

Suitable base salts are formed from bases which form non-toxic salts. Examples include the sodium, potassium, aluminium, calcium, magnesium, zinc, choline, diolamine, olamine, arginine, glycine, tromethamine, benzathine, lysine, meglumine and diethylamine salts. The compounds of the invention may also be formed as a zwitterion.

A suitable salt for amino acid compounds of the present invention is the hydrochloride salt. For a review on suitable salts see Stahl and Wermuth, Handbook of Pharmaceutical Salts: Properties, Selection, and Use, Wiley-VCH, Weinheim, Germany (2002).

Salts with quaternary ammonium ions can also be prepared with, for example, the tetramethyl-ammonium ion. Research has shown that the oral absorption of certain drugs may be increased by the preparation of "soft" quaternary salts. The quaternary salt is termed a "soft" quaternary salt since, unlike normal quaternary salts, e.g., R—N$^+$(CH$_3$)$_3$, it can release the active drug on hydrolysis. "Soft" quaternary salts have useful physical properties compared with the basic drug or its salts. Water solubility may be increased compared with other salts, such as the hydrochloride, but more important there may be an increased absorption of the drug from the intestine. Increased absorption is probably due to the fact that the "soft" quaternary salt has surfactant properties and is capable of forming micelles and unionized ion pairs with bile acids, etc., which are able to penetrate the intestinal epithelium more effectively. The pro-drug, after absorption, is rapidly hydrolyzed with release of the active parent drug.

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

Hereinafter all references to compounds of formula (I) include references to salts, solvates and complexes thereof and to solvates and complexes of salts thereof.

The compounds of the invention include compounds of formula (I) as hereinbefore defined, polymorphs, pro-drugs, and isomers thereof (including optical, geometric and tautomeric isomers) as hereinafter defined and isotopically-labeled compounds of formula (I).

As stated, the invention includes all polymorphs of the compounds of formula (I) as hereinbefore defined.

Also within the scope of the invention are so-called 'pro-drugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage or oxidative metabolism. Such derivatives are referred to as 'pro-drugs'. Further information on the use of pro-drugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Pro-drugs in accordance with the invention can, for example, be produced by replacing appropriate functionalities present in the compounds of formula (I) with certain moieties known to those skilled in the art as 'pro-moieties' as described in "Design of ester pro-drugs to enhance oral absorption of poorly permeable compounds" by K. Beaumont et al, Current Drug Metabolism, 2003 and "Design of Pro-drugs" by H. Bundgaard (Elsevier) 1985. Further, certain compounds of the invention may act as pro-drugs of other compounds of the invention. All protected derivatives, and pro-drugs, of the compounds of the invention are included within the scope of the invention.

Some examples of pro-drugs in accordance with the invention include:

(i) an ester of the carboxylic acid functionality (—COOH) of the compound of formula (I), for example, replacement of the hydrogen with (C$_1$-C6)alkyl, or a carboxamide thereof, for example, replacement of the hydroxyl with an amino functionality (—NH$_2$, —NHR or NRR' where R and R' each independently (C$_1$-C$_6$)alkyl);

(ii) an amide of the secondary amino functionality (NHR where R≠H) of the compound of formula (I), for example, replacement of the hydrogen with (C$_1$-C$_6$) alkanoyl.

Further examples of replacement groups in accordance with the foregoing examples and examples of other pro-drug types may be found in the aforementioned references, which are hereby incorporated by reference.

Aminoacyl-glycolic and -lactic esters are known as pro-drugs of amino acids (Wermuth C. G., *Chemistry and Industry*, 1980:433-435). The carbonyl group of the amino acids can be esterified by known means. Pro-drugs and soft drugs are known in the art (Palomino E., *Drugs of the Future*, 1990;15(4):361-368).

The invention also relates to therapeutic use of the present compounds as agents for treating or relieving the symptoms of neurodegenerative disorders. Such neurodegenerative disorders include, for example, Alzheimer's disease, Huntington's disease, Parkinson's disease, and Amyotrophic Lateral Sclerosis. The present invention also covers treating neurodegenerative disorders termed acute brain injury. These include but are not limited to: stroke, head trauma, and asphyxia. Stroke refers to a cerebral vascular disease and may also be referred to as a cerebral vascular accident (CVA) and includes acute thromboembolic stroke. Stroke includes both focal and global ischemia. Also, included are transient cerebral ischemic attacks and other cerebral vascular problems accompanied by cerebral ischemia. These vascular disorders may occur in a patient undergoing carotid endarterectomy specifically or other cerebrovascular or vascular surgical procedures in general, or diagnostic vascular procedures including cerebral angiography and the like. Other incidents are head trauma, spinal cord trauma, or injury from general anoxia, hypoxia, hypoglycemia, hypotension as well as similar injuries seen during procedures from embole, hyperfusion, and hypoxia. The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

The compounds of the present invention are useful for the general treatment of pain, particularly neuropathic pain.

Physiological pain is an important protective mechanism designed to warn of danger from potentially injurious stimuli from the external environment. The system operates through a specific set of primary sensory neurones and is exclusively activated by noxious stimuli via peripheral transducing mechanisms (Millan 1999 Prog. Neurobio. 57:1-164 for an integrative Review). These sensory fibres are known as nociceptors and are characterised by small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred after complex processing in the dorsal horn, either directly or via brain stem relay nuclei to the ventrobasal thalamus and then on to the cortex, where the sensation of pain is generated.

Intense acute pain and chronic pain may involve the same pathways driven by pathophysiological processes and as such cease to provide a protective mechanism and instead contribute to debilitating symptoms associated with a wide range of disease states. Pain is a feature of many trauma and disease states. When a substantial injury, via disease or trauma, to body tissue occurs the characteristics of nociceptor activation are altered. There is sensitisation in the periphery, locally around the injury and centrally where the nociceptors terminate. This leads to hypersensitivity at the site of damage and in nearby normal tissue. In acute pain these mechanisms can be useful and allow for the repair processes to take place and the hypersensitivity returns to normal once the injury has healed. However, in many chronic pain states, the hypersensitivity far outlasts the healing process and is normally due to nervous system injury. This injury often leads to maladaptation of the afferent fibres (Woolf & Salter 2000 Science 288: 1765-1768). Clinical pain is present when discomfort and abnormal sensitivity feature among the patient's symptoms. Patients tend to be quite heterogeneous and may present with various pain symptoms. There are a number of typical pain subtypes: 1) spontaneous pain which may be dull, burning, or stabbing; 2) pain responses to noxious stimuli are exaggerated (hyperalgesia); 3) pain is produced by normally innocuous stimuli (allodynia) (Meyer et al., 1994 Textbook of Pain 13-44). Although patients with back pain, arthritis pain, CNS trauma, or neuropathic pain may have similar symptoms, the underlying mechanisms are different and, therefore, may require different treatment strategies. Therefore pain can be divided into a number of different areas because of differing pathophysiology, these include nociceptive, inflammatory, neuropathic pain etc. It should be noted that some types of pain have multiple aetiologies and thus can be classified in more than one area, e.g. Back pain, Cancer pain have both nociceptive and neuropathic components.

Nociceptive pain is induced by tissue injury or by intense stimuli with the potential to cause injury. Pain afferents are activated by transduction of stimuli by nociceptors at the site of injury and sensitise the spinal cord at the level of their termination. This is then relayed up the spinal tracts to the brain where pain is perceived (Meyer et al., 1994 Textbook of Pain 13-44). The activation of nociceptors activates two types of afferent nerve fibres. Myelinated A-delta fibres transmitted rapidly and are responsible for the sharp and stabbing pain sensations, whilst unmyelinated C fibres transmit at a slower rate and convey the dull or aching pain. Moderate to severe acute nociceptive pain is a prominent feature of, but is not limited to pain from strains/sprains, post-operative pain (pain following any type of surgical procedure), posttraumatic pain, burns, myocardial infarction, acute pancreatitis, and renal colic. Also cancer related acute pain syndromes commonly due to therapeutic interactions such as chemotherapy toxicity, immunotherapy, hormonal therapy and radiotherapy. Moderate to severe acute nociceptive pain is a prominent feature of, but is not limited to, cancer pain which may be tumour related pain, (e.g. bone pain, headache and facial pain, visceral pain) or associated with cancer therapy (e.g. postchemotherapy syndromes, chronic postsurgical pain syndromes, post radiation syndromes), back pain which may be due to herniated or ruptured intervertabral discs or abnormalities of the lumber facet joints, sacroiliac joints, paraspinal muscles or the posterior longitudinal ligament Neuropathic pain is defined as pain initiated or caused by a primary lesion or dysfunction in the nervous system (IASP definition). Nerve damage can be caused by trauma and disease and thus the term 'neuropathic pain' encompasses many disorders with diverse aetiologies. These include but are not limited to, Diabetic neuropathy, Post herpetic neuralgia, Back pain, Cancer neuropathy, HIV neuropathy, Phantom limb pain, Carpal Tunnel Syndrome, chronic alcoholism, hypothyroidism, trigeminal neuralgia, uremia, or vitamin deficiencies. Neuropathic pain is pathological as it has no protective role. It is often present well after the original cause has dissipated, commonly lasting for years, significantly decreasing a patients quality of life (Woolf and Mannion 1999 Lancet 353:1959-1964). The symptoms of neuropathic pain are difficult to treat, as they are often heterogeneous even between patients with the same disease (Woolf & Decosterd 1999 Pain Supp. 6: S141-S147; Woolf and Mannion 1999 Lancet 353: 1959-1964). They include spontaneous pain, which can be continuous, or paroxysmal and abnormal evoked pain, such as hyperalgesia (increased sensitivity to a noxious stimulus) and allodynia (sensitivity to a normally innocuous stimulus).

The inflammatory process is a complex series of biochemical and cellular events activated in response to tissue injury or the presence of foreign substances, which result in swelling and pain (Levine and Taiwo 1994: Textbook of Pain 45-56). Arthritic pain makes up the majority of the inflammatory pain population. Rheumatoid disease is one of the commonest chronic inflammatory conditions in developed countries and rheumatoid arthritis is a common cause of disability. The exact aetiology of RA is unknown, but current hypotheses suggest that both genetic and microbiological factors may be important (Grennan & Jayson 1994 Textbook of Pain 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder 2002 Ann Pharmacother. 36:679-686; McCarthy et al., 1994 Textbook of Pain 387-395). Most patients with OA seek medical attention because of pain. Arthritis has a significant impact on psychosocial and physical function and is known to be the leading cause of disability in later life. Other types of inflammatory pain include but are not limited to inflammatory bowel diseases (IBD), Other types of pain include but are not limited to;

Musculo-skeletal disorders including but not limited to myalgia, fibromyalgia, spondylitis, sero-negative (non-rheumatoid) arthropathies, non-articular rheumatism, dystrophinopathy, Glycogenolysis, polymyositis, pyomyositis.

Central pain or 'thalamic pain' as defined by pain caused by lesion or dysfunction of the nervous system including but not limited to central post-stroke pain, multiple sclerosis, spinal cord injury, Parkinson's disease and epilepsy.

Heart and vascular pain including but not limited to angina, myocardial infarction, mitral stenosis, pericarditis, Raynaud's phenomenon, scieredoma, skeletal muscle ischemia.

Visceral pain, and gastrointestinal disorders. The viscera encompasses the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders include the functional bowel disorders (FBD) and the inflammatory bowel diseases (IBD). These GI disorders include a wide range of disease states that are currently only moderately controlled, including—for FBD, gastro-esophageal reflux, dyspepsia, the irritable bowel syndrome (IBS) and functional abdominal pain syndrome (FAPS), and—for IBD, Crohn's disease, ileitis, and ulcerative colitis, which all regularly produce visceral pain. Other types of visceral pain include the pain associated with dysmenorrhea, pelvic pain, cystitis and pancreatitis.

Head pain including but not limited to migraine, migraine with aura, migraine without aura cluster headache, tension-type headache.

Orofacial pain including but not limited to dental pain, temporomandibular myofascial pain.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

As a yet further aspect, there is provided a method for treating a disease selected from epilepsy, faintness attacks, hypokinesia, cranial disorders, neurodegenerative disorders, depression, anxiety, panic, pain, irritable bowel syndrome, sleep disorders, osteoarthritis, rheumatoid arthritis, neuropathological disorders, visceral pain, functional bowel disorders, inflammatory bowel diseases, pain associated with dysmenorrhea, pelvic pain, cystitis and pancreatitis comprising administering a therapeutically effective amount of a compound of formula (I) to a mammal in need of said treatment.

The biological activity of the alpha-2-delta ligands of the invention may be measured in a radioligand binding assay using [$^3$H]gabapentin and the $\alpha_2\delta$ subunit derived from porcine brain tissue (Gee N. S., Brown J. P., Dissanayake V. U. K., Offord J., Thurlow R., Woodruff G. N., *J. Biol. Chem.*, 1996;271:5879-5776). Results may be expressed in terms of μM or nM $\alpha2\delta$ binding affinity.

The compounds of the invention may also be administered in combination, separately, simultaneously or sequentially, with one or more other pharmacologically active agents. Suitable agents, particularly for the treatment of pain, include:

i) opioid analgesics, e.g. morphine, heroin, hydromorphone, oxymorphone, levorphanol, levallorphan, methadone, meperidine, fentanyl, codeine, dihydrocodeine, oxycodone, hydrocodone, propoxyphene, nalmefene, nalorphine, naloxone, naltrexone, buprenorphine, butorphanol, nalbuphine and pentazocine;

ii) opioid antagonists, e.g. naloxone, naltrexone iii) nonsteroidal antiinflammatory drugs (NSAIDs), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, and their pharmaceutically acceptable salts;

iv) barbiturate sedatives, e.g. amobarbital, aprobarbital, butabarbital, butabital, mephobarbital, metharbital, methohexital, pentobarbital, phenobartital, secobarbital, talbutal, theamylal, thiopental and their pharmaceutically acceptable salts;

v) benzodiazepines having a sedative action, e.g. chlordiazepoxide, clorazepate, diazepam, flurazepam, lorazepam, oxazepam, temazepam, triazolam and their pharmaceutically acceptable salts, vi) $H_1$ antagonists having a sedative action, e.g. diphenhydramine, pyrilamine, promethazine, chlorpheniramine, chlorcyclizine and their pharmaceutically acceptable salts;

vii) miscellaneous sedatives such as glutethimide, meprobamate, methaqualone, dichloralphenazone and their pharmaceutically acceptable salts;

viii) skeletal muscle relaxants, e.g. baclofen, carisoprodol, chlorzoxazone, cyclobenzaprine, methocarbamol, orphrenadine and their pharmaceutically acceptable salts, ix) NMDA receptor antagonists, e.g. dextromethorphan ((+)-3-hydroxy-N-methylmorphinan) and its metabolite dextrorphan ((+)-3-hydroxy-N-methylmorphinan), ketamine, memantine, pyrroloquinoline quinone and cis-4-(phosphonomethyl)-2-piperidinecarboxylic acid and their pharmaceutically acceptable salts;

x) alpha-adrenergic active compounds, e.g. doxazosin, tamsulosin, clonidine and 4-amino-6,7-dimethoxy-2-(5-methanesulfonamido-1,2,3,4-tetrahydroisoquinol-2-yl)-5-(2-pyridyl) quinazoline;

xi) tricyclic antidepressants, e.g. desipramine, imipramine, amytriptiline and nortriptiline;

xii) anticonvulsants, e.g. carbamazepine and valproate;

xiii) serotonin reuptake inhibitors, e.g. fluoxetine, paroxetine, citalopram and sertraline;

xiv) mixed serotonin-noradrenaline reuptake inhibitors, e.g. milnacipran, venlafaxine and duloxetine;

xv) noradrenaline reuptake inhibitors , e.g. reboxetine;

xvi) Tachykinin (NK) antagonists, particularly NK-3, NK-2 and NK-1 antagonists, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione 637), 5-[[(2R,3S)-2-[(1R)-1-[3,5-bis (trifluoromethyl)phenyl]ethoxy-3-(4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S)

xvii) Muscarinic antagonists, e.g oxybutin, tolterodine, propiverine, tropsium chloride and darifenacin;

xviii) COX-2 inhibitors, e.g. celecoxib, rofecoxib and valdecoxib;

xix) Non-selective COX inhibitors (preferably with GI protection), e.g. nitroflurbiprofen (HCT-1026);

xx) PDEV inhibitors, e.g. sildenafil, vardenafil (Bayer), tadalafil (Icos Lilly), 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine, 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one and 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one;

xxi) coal-tar analgesics, in particular, paracetamol;
xxii) neuroleptics, such as droperidol;
xxiii) Vanilloid receptor agonists, e.g. resinferatoxin;
xxiv) Beta-adrenergic compounds such as propranolol;
xxv) Local anaesthetics, such as mexiletine;
xxvi) Corticosteriods, such as dexamethasone
xxvii) serotonin receptor agonists and antagonists;
xxviii) cholinergic (nicotinic) analgesics; and
xxix) miscellaneous agents such as Tramadol®.

Thus, the invention further provides a combination comprising a compound of formula (I) or a pharmaceutically acceptable salt, solvate or pro-drug thereof, and a compound or class of compounds selected from the group (i)-(xxix), above. There is also provided a pharmaceutical composition comprising such a combination, together with a pharmaceutically acceptable excipient, diluent or carrier, particularly for the treatment of a disease for which an alpha-2-delta ligand is implicated.

Thus, as a further aspect, the invention provides a combination product comprising a compound of formula (I), or a pharmaceutically acceptable salt thereof, and a PDEV inhibitor. Preferably, the PDEV inhibitor is selected from sildenafil, vardenafil, tadalafil, 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine, 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one and 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one.

Combinations of the compounds of the present invention and other therapeutic agents may be administered separately, sequentially or simultaneously.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

The compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose. Suitable formulations of the compounds of the invention may be in hydrophilic or hydrophobic matrix, ion-exchange resin complex, coated or uncoated form and other types as described in U.S. Pat. No. 6,106,864 as desired.

Compounds of the invention may be administered alone or in combination with one or more other drugs (or as any combination thereof). Generally they will be administered as a formulation in association with one or more suitable pharmaceutically acceptable excipient(s). The term "excipient" is used herein to describe any ingredient other than the compound of the invention. The choice of excipient will to a large extent depend on the particular mode of administration, the effect of the excipient on solubility and stability, and the nature of the dosing form. If appropriate, auxiliaries can be added. Auxiliaries are preservatives, anti-oxidants, flavours or colourants.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

The compounds of the present invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, multi- and nano-particulates, gels, films (incl. muco-adhesive), powder, ovules, elixirs, lozenges (incl. liquid-filled), chews, solid solution, liposome, suspensions, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be administered as osmotic dosage form, or in the form of a high energy dispersion or as coated particles or fast-dissolving, fast-disintegrating dosage form as described in Expert Opinion in Therapeutic Patents, 11(6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid compositions for oral administration may be formulated to be immediate and/or modified release. Modified release compositions include delayed-, sustained-, pulsed-, controlled-, targeted and programmed release. Suitable modified release compositions for the purpose of the invention are described in U.S. Pat. No. 6,106,864. Details of other suitable release technologies such as high energy dispersions and osmotic and coated particles are to be found in Verma et al., Pharmaceutical Technology On-line, 25(2), 1-14 (2001).

Solid compositions of a similar type may also be employed as fillers in capsules such as gelatin, starch or HPMC capsules. Preferred excipients in this regard include lactose, starch, a cellulose, milk sugar or high molecular weight polyethylene glycols. Liquid compositions may be employed as fillers in soft or hard capsules such as gelatin capsule. For aqueous and oily suspensions, solutions, syrups and/or elixirs, the compounds of the invention may be combined with various sweetening or flavouring agents, colouring matter or dyes, with emulsifying and/or suspending agents and with diluents such as water, ethanol, propylene glycol, methylcellulose, alginic acid or sodium alginate, glycerin, oils, hydrocolloid agents and combinations thereof. Moreover, formulations containing these compounds and excipients may be presented as a dry product for constitution with water or other suitable vehicles before use.

The compounds of the present invention can also be administered by injection, that is, intravenously, intramuscularly, intracutaneously, intraduodenally, or intraperitoneally, intraarterially, intrathecally, intraventricularly, intraurethrally, intrasternally, intracranially, intraspinally or subcutaneously, or they may be administered by infusion, needle (including micro-needle) injectors, needle-free injectors or implant injection techniques. For such parenteral administration they are typically used in the form of a sterile aqueous solution, suspension or emulsion (or system so that can include micelles) which may contain other substances known in the art, for example, enough salts or carbohydrates such as glucose to make the solution isotonic with blood. The aqueous solutions should be suitably buffered (preferably to a pH of from 3 to 9), if necessary. For some forms of parenteral administration they may be used in the form of a sterile non-aqueous system such as fixed oils, including mono- or diglycerides, and fatty acids, including oleic acid. The preparation of suitable parenteral formulations under sterile conditions for example lyophilisation is readily accomplished by standard pharmaceutical techniques well-known to those skilled in the art. Alternatively, the active ingredient may be in powder form for constitution with a suitable vehicle (e.g. sterile, pyrogen-free water) before use.

The solubility of compound of formula (I) used in the preparation of parenteral solutions may be increased by the use of appropriate formulation techniques, such as the incorporation of solubility-enhancing agents.

Compositions for parenteral administration may be formulated to be immediate and/or modified release. Thus compounds of the invention may be formulated in a more solid form for administration as an implanted depot providing long-term release of the active compound.

The compounds of the present invention can also be administered intranasally or by inhalation. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomiser (preferably an atomiser using electrohydrodynamics to produce a fine mist) or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide, a further perfluorinated hydrocarbon such as Perflubron (trade mark) or other suitable gas. For intranasal use, the powder may comprise a bioadhesive agent, for example, chitosan or cyclodextrin.

In the case of a pressurised aerosol, the dosage unit may be determined by providing a valve to deliver a metered amount. The pressurised container, pump, spray, atomiser or nebuliser contains a solution or suspension of the compounds of the invention comprising, for example, ethanol (aqueous ethanol) or a suitable agent for dispersing, solubilising or extending release and a propellant(s) as the solvent, which may additionally contain a lubricant, e.g. sorbitan trioleate or an oligolactic acid.

Prior to use in a dry powder formulation or suspension formulation for inhalation the compounds of the invention will be micronised to a size suitable for delivery by inhalation (typically considered as less than 5 microns). Micronisation could be achieved by a range of methods, for example spiral jet milling, fluid bed jet milling, use of supercritical fluid processing to form nanoparticles, high pressure homogenisation or by spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of the invention, propylene glycol, sterile water, ethanol and sodium chloride. Alternative solvents which may be used in place of propylene glycol include glycerol or polyethylene glycol.

Suitable flavours, such as menthol and levomenthol, or sweeteners, such as saccharin or saccharin sodium, may be added to those formulations of the invention intended for inhaled/intranasal administration.

Compositions for inhaled/intranasal administration may be formulated to be immediate and/or modified release using, for example, poly(DL)-lactic-coglycolic acid (PGLA). Modified release compositions include delayed-, sustained-, pulsed-, controlled-, targeted and programmed release.

Alternatively, the compounds of the invention may be administered topically to the skin or mucosa, that is, dermally or transdermally. Typical formualtions for this purpose include gels, hydrogels, lotions, solutions, creams, ointments, dusting powders, dressings, foams, films skin patches, wafers, implants, sponges, fibres, bandages and microemulsions. Liposomes may also be used. For such applications, the compounds of the invention can be suspended or dissolved in, for example, a mixture with one or more of the following: mineral oil, liquid petrolatum, white petrolatum, propylene glycol, polyoxyethylene polyoxypropylene compound, emulsifying wax, fixed oils, including synthetic mono- or diglycerides, and fatty acids, including oleic acid, water, sorbitan monostearate, a polyethylene glycol, liquid paraffin, polysorbate 60, cetyl esters wax, cetearyl alcohol, 2-octyidodecanol, benzyl alcohol, alcohols such as ethanol. Penetration enhancers may be incorporated—see for example, J. Pharm. Sci., 88(10), 955-958 by Finnin and Morgan (October 1999). The following may also be used; polymers, carbohydrates, proteins and phospholipids in the form of nanoparticles (such as niosomes or liposomes).

Other means of topical administration include delivery by iontophoresis, electroporation, phonophoresis, sonophoresis and needle-free or microneedle injection (e.g. Powderject™, Bioject™ etc.).

Compositions for topical administration may be formulated to be immediate and/or modified release. Modified release compositions include delayed-, sustained-, pulsed-, controlled-, targeted and programmed release.

Alternatively, the compounds of the invention can be administered rectally, for example in the form of a suppository, pessary or enema. They may also be administered by vaginal route. For example, these compositions may be prepared by mixing the drug with a suitable non-irritant excipient(s), such as cocoa butter, synthetic glyceride esters or polyethylene glycols, which are solid at ordinary temperatures, but liquefy and/or dissolve in the cavity to release the drug.

Compositions for rectal/vaginal administration may be formulated to be immediate and/or modified release. Modified release compositions include delayed-, sustained-, pulsed-, controlled-, targeted and programmed release.

The compounds of the invention may also be administered directly to the eye or ear, typically in the form of drops of a micronised suspension or solution in isotonic, pH adjusted, sterile saline. Other formulations suitable for ocular and aural administration include ointments, bio-degradable (e.g. absorbable gel sponges, collagen) or non-biodegradable (e.g. silicone) implants, wafers, lenses and particulate or vesicular systems such as niosomes or liposomes. A polymer, such as crossed-linked polyacrylic acid, polyvinylalcohol, hyaluronic acid, a cellulosic polymer (e.g. hydroxypropylmethylcellulose, hydroxyethylcellulose, methyl cellulose), or a heteropolysaccharide polymer (e.g. gelan gum) may be incorporated together a preservative, such as benzalkonium chloride. Such formulations may also be delivered using iontophoresis.

Compositions for ocular/aural administration may be formulated to be immediate and/or modified release. Modified release compositions include delayed-, sustained-, pulsed-, controlled-, targeted and programmed release.

The compounds of the invention may also be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are generally useful for most dosage forms and administration routes. Both inclusion and non-inclusion complexes may be used. As an alternative to direct complexation with the drug the cyclodextrin may be used as an auxiliary additive, i.e. as a carrier, diluent or solubiliser. Alpha-, beta- and gamma-cyclodextrins are most commonly used and suitable examples are described in WO-A-91/11172, WO-A-94/02518 and WO-A-98/55148.

The term 'administered' includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, lipsomes, immunoliposomes, lipofectin, cationic facial amphiphiles (CFAs) and combinations thereof. The routes for such delivery mechanisms include but are not limited to mucosal, nasal, oral, parenteral, gastrointestinal, topical or sublingual routes.

Accordingly, the present invention provides a pharmaceutical composition comprising a compound of formula (I) or a pharmaceutically acceptable salt, solvate, polymorph or prodrug thereof, together with a pharmaceutically acceptable excipient, diluent or carrier.

The element of the pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form. The quantity of active component in a unit dose preparation may be varied or adjusted from 0.1 mg to 1 g according to the particular application and the potency of the active components. In medical use the drug may be administered one to three times daily as, for example, capsules of 100 or 300 mg. In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages are based on an average human subject having a weight of about 65 kg to 70 kg. The physician will readily be able to determine doses for subjects whose weight falls outside this range, such as infants and the elderly. The dosages, however, may be varied depending upon the requirements of the patient, the severity of the condition being treated, and the compounds being employed. Determination of the proper dosage for a particular situation is within the skill of the art. Generally, treatment is initiated with smaller dosages which are less than the optimum dose of the compounds. Thereafter, the dosage is increased by small increments until the optimum effect under the circumstances is reached. For convenience, the total daily dosage may be divided and administered in portions during the day, if desired.

The pharmaceutical composition according to the present invention can, if desired, also contain one or more compatible therapeutic agents. In particular, the composition can be combined with any one or more compounds useful in the treatment of pain, such as those listed above. Thus, the present invention presents a pharmaceutical composition comprising a compound of formula (I), one or more other pharmacologically active agents and one or more pharmaceutically acceptable carriers.

For the avoidance of doubt, references herein to 'treatment' include references to curative, palliative and prophylactic treatment.

General Methods

The compounds of formula (I) can be synthesised using the various methods set out below:

According to the first process, (A), a compound of formula (I) may be prepared by deprotection of a compound of formula (II), (III) or (IV)

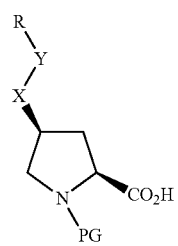
(II)

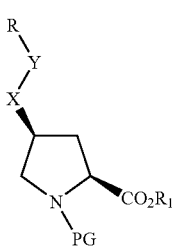
(III)

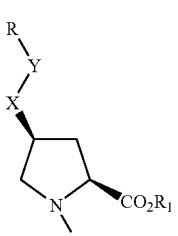
(IV)

where R, X and Y are as described for formula (I), $R_1$ is a suitable carboxylic acid protecting group, such as $C_{1-6}$ alkyl, and PG is a suitable protecting group such as tert-butoxycarbonyl, by conventional methods, e.g. acid mediated hydrolysis using a strong acid, such as trifluoroacetic acid or hydrochloric acid, in a suitable solvent, such as dioxan or dichloromethane.

Compounds of formula (I) may be prepared directly from compounds of formula (III) by hydrolytic cleavage.

Compounds of formula (II) may be prepared by hydrolysis of the ester functionality of compound (III),

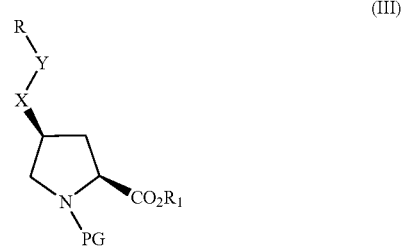
(III)

where X, Y, R, PG and $R_1$ are as defined above and hydrolysis is facilitated by an alkali metal hydroxide, such as lithium hydroxide, in a suitable solvent, such as aqueous dioxan.

Compounds of formula (III) can be formed by the following methods:

i) Reaction of a compound of formula (VI)

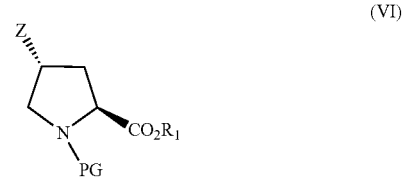
(VI)

where Z is a suitable leaving group, such as mesylate, tosylate, triflate or halo, with a compound RYX—H, using a suitable base, such as an alkali metal salt, such as $K_2CO_3$ or an alkali metal hydride, such as NaH, in a suitable solvent, such as DMF, at a temperature of 20-140° C.

ii) Where RYX— is ArO—, where Ar is an optionally substituted aryl or heteroaryl ring, reaction of a compound of formula (VII)

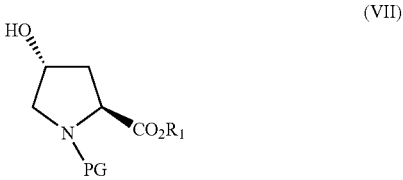
(VII)

with a compound of formula ArOH, using Mitsunobu conditions of a suitable azidodicarboxylate, such as DIAD and triphenylphosphine or tributylphosphine in a suitable solvent, such as THF, at a temperature of 25-60° C.

iii) Hydrogenolysis of a compound of formula (VIII)

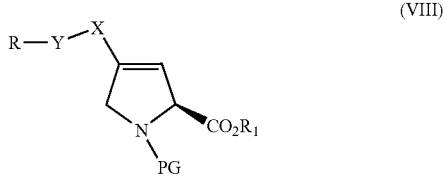
(VIII)

with a suitable catalyst such as palladium on carbon.

Compounds of formula (VIII) can be prepared from compounds of formula (XII) by addition of an organometallic in the presence of a suitable catalyst and additives e.g., addition of benzylzinc bromide in the presence of NBu$_4$I, a palladium catalyst and a phosphine ligand in a suitable solvent such as 1:1 THF: 1-methyl-2-pyrollidinone.

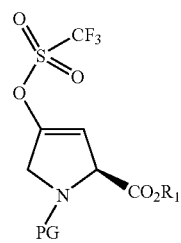

(XII)

Compounds of formula (XII) are prepared from compounds of formula (X) by the addition of a suitable base followed by a triflating agent e.g., addition of n-butyl lithium at −78° C.−−20° C. in a suitable solvent such as THF followed by the addition of triflic anhydride.

iv) Where X is Ch$_2$, hydrogenolysis of a compound of formula (IX)

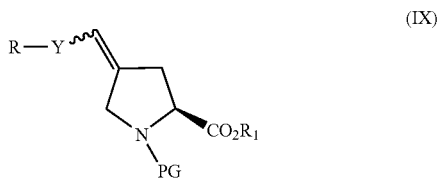

(IX)

with a suitable catalyst such as palladium on carbon.

Compounds of the formula (IX) can be prepared from compounds of the formula (X) using the Wittig reaction in which the ylide is formed from a suitable phosphonium salt and a base such as 1M tBuOK/THF or sodium t-amylate in toluene or dichloromethane at room temperature.

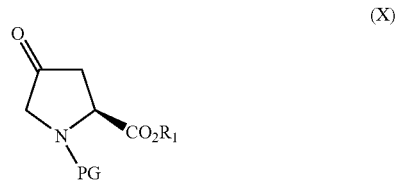

(X)

Compounds of the formula (IX) are hydrolysed to compounds of the formula (XVII) under basic conditions such as aq. lithium hydroxide in THF/H$_2$O. Compounds of the formula (XVIII) are prepared from (XVII) using standard coupling reagents such as DCC, DMAP and a suitable alcohol such as menthol (R$_2$) in dichloromethane at room temperature.

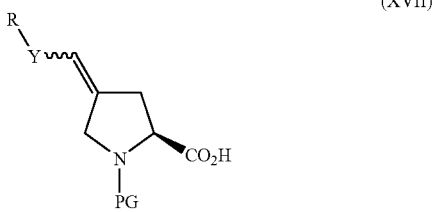

(XVII)

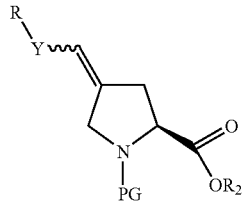

(XVIII)

Compounds of the formula (XVIII) are hydrogenated 1-18 h under a hydrogen atmosphere of 15 psi at room temperature using a suitable catalyst such as PtO$_2$ in EtOAc and/or toluene to give compounds of the formula (XIV).

Compounds of the formula (XIV) are globally deprotected according to the method of Process A, suitably using 6M hydrochloric acid for 18 h at 60° C.-120° C., to furnish compounds of the formula (I), where X is CH$_2$.

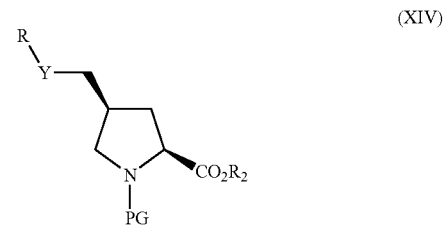

(XIV)

Alternatively, compounds of formula (VIII) and (IX) can be prepared by dehydration of compounds of the formula (XI) by acid catalysed dehydration.

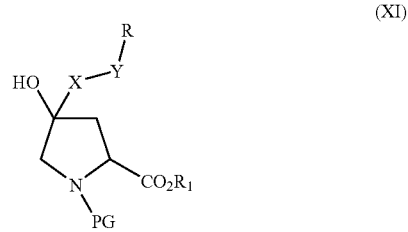

(XI)

Compounds of the formula (XI) can be prepared by addition of an organometallic to compounds of the formula (VIII), e.g., addition of benzylmagnesium bromide to VIII in a suitable solvent, such as THF, at a temperature of −78° C.-20° C.

v) Where Y is O and X is CH$_2$, reaction of a compound of formula (XVI)

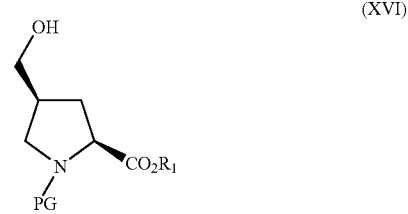

(XVI)

with a compound of formula R—OH, using Mitsunobu conditions.

Compounds of formula (XVI) can be prepared by hydroboration of compounds of formula (XV).

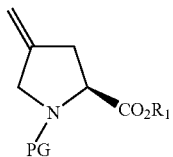
(XV)

Compounds of formula (XV) can be prepared from compounds of formula (XIII) by hydrolysis of the ester functionality to give compounds of formula (XIV), followed by re-esterification.

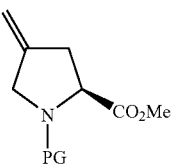
(XIII)

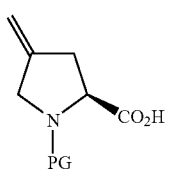
(XIV)

Compounds of formula (XIII) can be prepared from compounds of formula (X) using a suitable methylene Wittig reagent such as methyltriphenylphosphonium bromide and a base such as potassium t-butoxide in a suitable solvent e.g. toluene.

Compounds of formula (XVI) may also be prepared by reduction of carboxylic acids of formula (XVII) using a hydroborating agent such as $BH_3$ in a suitable solvent such as THF at a temperature of 0-30° C.

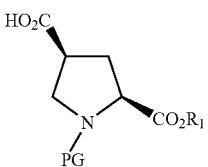
(XVII)

Compounds of formula (XVII) may be prepared by aromatic oxidation of compounds of formula (XVIII) using suitable conditions such as ruthenium chloride and sodium periodate in a solvent mixture such as $H_2O$, EtOAc and $CH_3CN$ at room temperature.

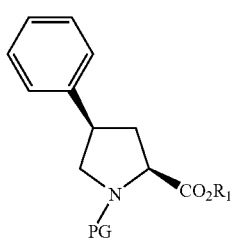
(XVIII)

Referring to the general methods above, it will be readily understood to the skilled person that where protecting groups are present, these will be generally interchangeable with other protecting groups of a similar nature, e.g. where an amine is described as being protected with a tert-butoxycarbonyl group, this may be readily interchanged with any suitable amine protecting group.

The present invention is illustrated by the following non-limiting examples and intermediates, where the following abbreviations are used:

| | |
|---|---|
| THF | Tetrahydrofuran |
| DMF | Dimethylformamide |
| DIAD | Diisopropyl azodicarboxylate |
| EtOAc | Ethyl acetate |
| DCM | Dichloromethane |
| rt | Room temperature |
| MeOH | Methanol |
| EtOH | Ethanol |
| TFA | Trifluoroacetic acid |
| BOC | tert butyloxycarbonyl |

EXAMPLE 1

(2S,4S)-4-(Benzylsulfanyl)-pyrrolidine-2-carboxylic acid

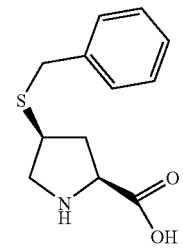

To a solution of (2S,4S)-4-Benzylsulfanyl-pyrrolidine-1,2-dicarboxylic acid di-tert-butyl ester (Preparation 2, 130 mg, 3.3 mmol) in dichloromethane (2.5 ml) was added trifluoroacetic acid (2.5 ml) and the mixture stirred at room temperature under a nitrogen atmosphere for 36 hours. The solvent was removed under reduced pressure and the residue purified by ion-exchange chromatography using Dowex™ 50WX8-200 resin eluting first with water and then with 10% aq ammonia to give the title compound (66 mg, 75%) as a white solid.
$^1$H-NMR (400 MHz, $D_2O$) δ=1.88-1.98 (1H, m); 2.45-2.56 (1H, m); 3.07-3.13 (1H, m); 3.22-3.38 (2H, m); 3.66-3.74 (2H, s); 3.93-4.01 (1H, m); 7.11-7.29 (5H, m) LRMS (electrospray): m/z [MH$^+$] 238; [MNa+] 260; [MH$^-$] 236 Microanalysis: Found C, 59.36; H, 6.33; N, 5.77. $C_{12}H_{15}NO_2S$. 0.3 $H_2O$ requires C, 59.38; H, 6.48; N, 5.77.

EXAMPLE 2

(2S,4S)-4-[(4-chlorobenzyl)oxyl]-pyrrolidine-2-carboxylic acid

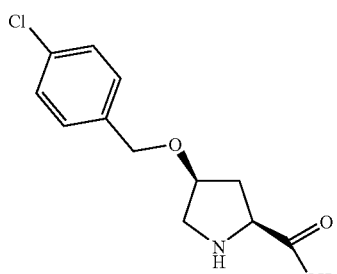

(2S,4S)-1-(tert-butoxycarbonyl)-4-[(4-chlorobenzyl)oxy]-2-pyrrolidinecarboxylic acid (Preparation 4, 96 mg, 0.38 mmol) was dissolved in dichloromethane (5 ml). Trifluoroacetic acid (5 ml) was added and the mixture left overnight at room temperature. The reaction mixture was partitioned between dichloromethane (25 ml) and water (25 ml). The aqueous layer was separated, washed with more dichloromethane (25 ml) and evaporated to dryness. The product was purified using Dowex™ 50WX8-200 resin, eluting first with water then 9:1 water:ammonia yielding the title compound (5 mg, 5% yield) as a white solid.

$^1$H-NMR (400 MHz, CD$_3$OD) δ=2.4-2.5(m, 1H), 2.6-2.7 (m, 1H), 3.4-3.5(m, 1H), 3.6-3.7(m, 1H), 4.5-4.7(m, 4H), 7.3-7.5(m, 4H). LCMS (electrospray): m/z [M⁻] 254

EXAMPLE 3

(2S,4S)-4-[(4-bromophenylthio]-pyrrolidine-2-carboxylic acid

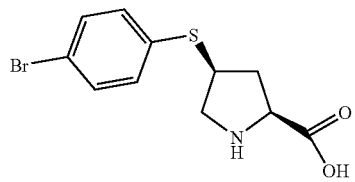

(2S,4S)-4-(4-Bromo-phenylsulfanyl)-pyrrolidine-1,2-dicarboxylic acid 1-tert-butyl ester (Preparation 7, 54 mg, 0.14 mmol) was dissolved in 4M HCl in dioxan and stirred for 2h at rt. The solvent was removed in vacuo to give a cream solid (32 mg, 76%).

$^1$H-NMR (400 MHz, CD$_3$OD) δ=2.20 (1H, m), 2.83 (1H, m), 3.32 (1H, m), 3.70 (1H, m), 4.15 (1H, m), 4.50 (1H, m), 7.40 (2H, d), 7.55 (2H, m). LRMS (electrospray): m/z [MH⁺] 302, 304. Microanalysis: Found C, 39.01; H, 4.23; N, 4.14. C$_{11}$H$_{12}$NO$_2$SBr. 0.9 HCl requires C, 39.44; H, 3.88; N, 4.18.

EXAMPLE 4

(2S,4S)-4-phenylthio-pyrrolidine-2-carboxylic acid

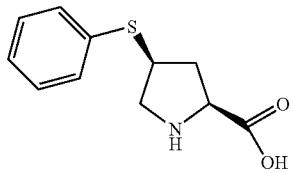

The title compound was made by the method of Example 3 starting from the title compound of Preparation 8. The yield was 60% and the title compound was a white solid.

$^1$H-NMR (400 MHz, CD$_3$OD) δ=2.19 (1H, m), 2.80 (1H, m), 3.34 (1H, m), 3.70 (1H, m). 4.10 (1H, m), 4.56 (1H, m), 7.030-7.60 (5H, m). LCMS (Electrospray): m/z [MH⁺] 224. Microanalysis: Found C, 48.95; H, 5.50; N, 4.97. C$_{11}$H$_{13}$NO$_2$S. HCl. 0.5H$_2$O requires C, 49.16; H, 5.63; N, 5.21.

EXAMPLE 5

(2S,4S)-4-[2-fluorophenoxy]-pyrrolidine-2-carboxylic acid

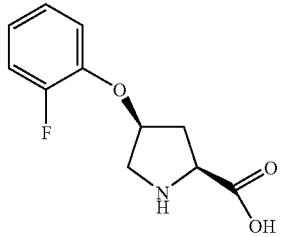

The title compound was made by the method of Example 3 in 74% yield starting from the title compound from preparation 10.

$^1$H-NMR (400 MHz, MeOD): δ=2.60-2.76 (m, 2H), 3.57-3.65 (m, 1H), 3.75 (d, 2H), 4.56-4.64 (m, 1H), 4.85 (s, 3H), 5.18-5.24 (m, 1H), 6.98-7.19 (m, 4H). LRMS (electrospray): [M−1] 224, [MH⁺] 226. Microanalysis: Found: C, 50.38; H, 4.95; N, 5.29% C$_{11}$H$_{12}$FNO$_3$ requires C, 50.49; H, 5.01, N, 5.35%.

EXAMPLE 6

(2S,4S)-4-[(4-chlorophenoxy)-pyrrolidine-2-carboxylic acid

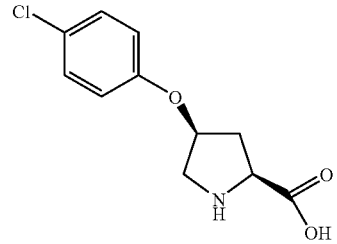

The BOC protected product (250 mg, 0.73 mmol) from Preparation 12 was stirred in 4M HCl in dioxan (5 ml) at 0° C. for 2 hours. Diethylether (10 ml) was added and the resultant precipitate filtered off and washed with diethylether to give the title compound (178 mg, 87%).

$^1$H-NMR (400 MHz, MeOD): δ=2.59-2.71 (m, 2H), 3.56-3.72 (m, 2H), 4.57-4.66(m, 1H), 4.82-4.93 (M, 3H), 5.17-5.25 (m, 1H), 6.88-6.98 (m, 2H), 7.26-7.36 (m, 2H). LRMS (Electrospray): [M−1] 240, [MH+] 242, [MNa+] 264. Microanalysis: Found: C, 47.48; H, 4.71; N, 4.92. C$_{11}$H$_{12}$ClNO$_3$.HCl requires C, 47.50; H, 4.71; N, 5.04%.

EXAMPLE 7

(2S,4S)-4-[2-isoquinolinoxy]-pyrrolidine-2-carboxylic acid

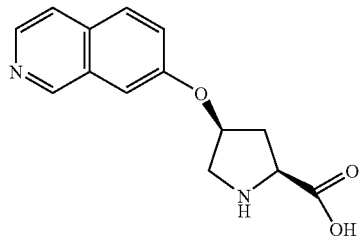

(2S,4S)-4-(Isoquinolin-7-yloxy)-pyrrolidine-1,2-dicarboxylic acid 1-tert-butylester (Preparation 13, 120 mg, 0.29 mmol) was stirred in TFA (3 ml) for 4.5 hours at room temperature. The solvent was removed in vacuo and triturated with diethyl ether to give an extremely hygroscopic solid which was redissolved in 2N HCl (3 ml) and stirred at room temperature for one hour. The solution was washed once with diethylether (5 ml) and the aqueous evaporated to give a foam. Trituration with ether gave the title compound as a glass (24 mg, 28%).

$^1$H-NMR (400 MHz, CH$_3$OD): δ=2.68-2.80(m, 1H), 2.82-2.97 (m, 1H), 3.75-3.91 (m, 2H), 4.62-4.75 (m, 1H), 4.75-4.96 (m, 5H exchangeable), 5.48-5.60 (m, 1H), 775-7.81 (m, 1H), 7.98-8.02 (m, 1H), 8.26 (d, 1H), 8.39-8.55 (m, 2H), 9.64 (s, 1H) LRMS (Electrospray) [M−1] 257, [MH$^+$] 259

EXAMPLE 8

(2S,4S)-4-(3-Chloro-phenoxy)-pyrrolidine-2-carboxylic acid

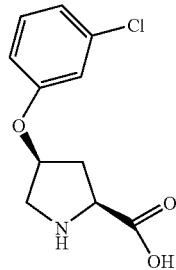

A solution of preparation 15 (29.25 mol) was dissolved in THF (20 L) & filtered. To this solution was added 4M HCl in dioxane (30 L) & stirred overnight. Tert-Butyl methyl ether (70 L) was added to the resultant suspension & the product was collected by filtration (7.06 kg, 86.7%).

$^1$H NMR (400 MHz, CD$_3$OD): δ=2.65 (m, 2H), 3.60 (dd, 1H), 3.70 (d, 1H), 4.60 (dd, 1H), 5.02 (m, 1H), 6.88 (m, 1H), 6.97 (s, 1 H), 7.03 (d, 1H), 7.29 (dd, 1H). LRMS (Electrospray [MH$^+$] 242, [M−1] 240. Microanalysis: Found, C, 46.97; H, 4.70; N, 4.90. C$_{11}$H$_{12}$ClNO$_3$.HCl.0.1H$_2$O requires C, 47.20; H, 4.75; N, 5.00.

EXAMPLE 9

(2S,4S)-4-(Benzyloxy)-pyrrolidine-2-carboxylic acid

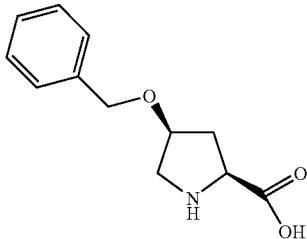

(2S,4S)-1-(tert-butoxycarbonyl)-4-(benzyloxy)-pyrrolidine-2-carboxylic acid (Preparation 17, 150 mg, 0.47 mmol) was dissolved in dichloromethane (5 ml). Trifluoroacetic acid (5 ml) was added and the mixture left stirring overnight at room temperature. The reaction mixture was partitioned between dichloromethane (25 ml) and water (25 ml). The aqueous layer was separated, washed with more dichloromethane (25 ml) and evaporated to dryness. The product was purified using an ion exchange column (Dowex 50WX8-200 resin), eluting first with water then 9:1 water:ammonia yielding the title compound (34 mg, 33% yield) as a white solid.

$^1$H-NMR (400 MHz, CD$_3$OD) δ=2.3-2.5 (m, 1H), 3.1-3.18 (m, 1H), 3.4-3.5 (d, 1H), 3.9-3.95(m, 1H), 4.2 (s, 1H), 4.4-4.55 (dd, 3H), 7.2-7.4 (m, 5H). LCMS (Electrospray): m/z [MNa$^+$] 244.

EXAMPLE 10

(2S,4S)-4-(3-Fluoro-benzyl)-pyrrolidine-2-carboxylic acid mono hydrochloride salt

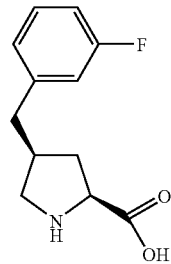

4-(3-Fluoro-benzyl)-pyrrolidine-1,2-dicarboxylic acid 1-tert-butyl ester 2-(2-isopropyl-5-methyl-cyclohexyl)ester (Preparation 35, 0.91 g, 1.96 mmol) was dissolved in toluene (2 ml). 6N hydrochloric acid (50 ml) was added and stirred at reflux for 18 h. The reaction mixture was cooled to room temperature and extracted with ethyl acetate (3×20 ml). The aqueous layer was concentrated by evaporated under reduced pressure to give the title compound (417 mg, 81%) as a white solid. $^1$H-NMR showed a 7:1 ratio of cis:trans diastereoisomers so the product was recrystallised from isopropyl alcohol to give the title compound (170 mg, 65%) in a ratio of 14:1 cis:trans as determined by NMR.

$^1$H-NMR (400 MHz, CD$_3$OD): (mixture of diastereoisomers 2S,4S:2S,4R (14:1)): δ=1.85 (q, 1H), 2.51 (quin, 1H), 2.69-2.85 (m, 3H), 3.07 (t, 1H), 3.41 (dd, 1H), 4.38 and 4.48 (t, 1H), 6.90-7.04 (m, 3H), 7.32 (q, 1H). LRMS (APCI): m/z [MH]$^+$ 224. [α]$_D$$^{25}$ −1.27° (c=9.00 in methanol). Microanalysis: Found C, 55.56; H, 5.81; N, 5.34%. C$_{12}$H$_{14}$FNO$_2$.HCl requires C, 55.50; H, 5.82; N, 5.39%.

EXAMPLE 11

(2S,4S)-4-(2.3-Difluoro-benzyl)-pyrrolidine-2-carboxylic acid mono-hydrochloride salt

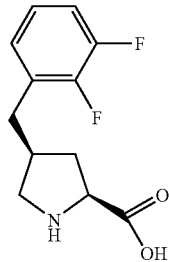

The title compound was made from by the method of Example 10, starting from the title compound of Preparation 37, and purified by re-crystallisation with acetone/ether to give the title compound as a mixture of diastereoisomers (2S,4S:2S,4R (12:1)) determined by $^1$H-NMR (500 mg, 60%) as a white solid.

$^1$H-NMR (400 MHz, CD$_3$OD) (mixture of diastereoisomers cis:trans (12:1)): δ=0.80-1.90 (m, 0.92H), 2.12-2.20 (m, 0.08H), 2.28-2.36 (m, 0.08H), 2.49-2.58 (q, 0.92H), 2.66-

2.81 (m, 1H), 2.83-2.95 (m, 2H), 3.02-3.13 (t, 1H), 3.46 (dd, 1H), 4.40 (dd, 0.92H), 4.48-4.54 (m, 0.08H), 7.03-7.20 (m, 3H). LRMS (Electrospray): m/z [M+H]+242. Microanalysis: Found C, 51.42; H, 5.08; N, 5.01%. $C_{12}H_{13}NO_2F_2$·HCl requires C, 51.90; H, 5.08; N, 5.04%.

EXAMPLE 12

(2S,4S)-4-(2,5-Difluoro-benzyl)-pyrrolidine-2-carboxylic acid mono hydrochloride salt

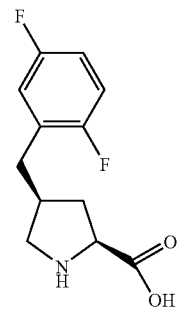

The title compound was made by the method of Example 10, starting from the title compound of Preparation 36.

$^1$H-NMR (400 MHz, CD$_3$OD): (mixture of diastereoisomers 2S,4S:2S,4R (26:1)): δ=1.86 (q, 1H), 2.51-2.54 (m, 1H), 2.75-2.83 (m, 3H), 3.09 (t, 1H), 3.45 (q, 1H), 4.39 and 4.49 (2t, 1H) 26:1, 7.00-7.14 (m, 3H). LRMS (APCI): m/z [MH]+242. Microanalysis: Found C, 50.18; H, 4.94; N, 4.83%. $C_{12}H_{13}F_2NO_2$·HCl requires C, 51.90; H, 5.08; N, 5.04%. $[α]_D^{25}$ −0.22° (c=1.84 in methanol).

EXAMPLE 13

(2S,4S)-4-Cyclohexylmethyl-pyrrolidine-2-carboxylic acid mono hydrochloride salt

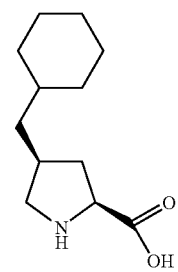

4-Cyclohexylmethyl-pyrrolidine-1,2-dicarboxylic acid 1-tert-butyl ester 2-(2-isopropyl-5-methyl-cyclohexyl)ester (Preparation 38, 316 mg, 0.70 mmol) was dissolved in toluene (2 ml). 6N hydrochloric acid (50 ml) was added and stirred at reflux for 72 hours. The reaction mixture was cooled to room temperature and extracted with ethyl acetate (3×20 ml). The aqueous layer was concentrated by evaporation under reduced pressure to give the title compound as a white solid (80 mg, 48%).

$^1$H-NMR (400MHz, CD$_3$OD): (mixture of diastereoisomers 2S,4S:2S,4R (6:1)): δ=0.83-1.00 (m, 2H), 1.13-1.40 (m, 6H), 1.62-1.81 (m, 6H), 2.48 (m, 2H), 2.90 (t, 1H), 3.48 (t, 1H), 4.32 and 4.42 (2t, 1H). LRMS (APCI): m/z [MH]+ 212. $[α]_D^{25}$ −1.86° (c=2.04 in methanol).

EXAMPLE 14

(2S,4S)-4-(3-Methoxy-benzyl)-pyrrolidine-2-carboxylic acid mono hydrochloride salt

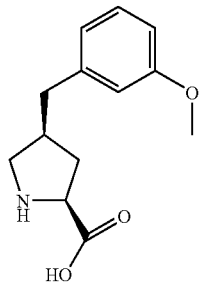

The title product was made by the method of Example 10, starting from the title compound of Preparation 39.

$^1$H-NMR (400 MHz, CD$_3$OD): (mixture of diastereoisomers 2S,4S:2S,4R (15:1)): δ=1.79-1.89 (m, 1H), 2.47-2.52 (m, 1H), 2.68-2.77 (m, 3H), 3.06 (t, 1H), 3.36 (t, 1H), 3.39 (s, 3H), 4.37 and 4.47 (t, 1H), 6.81 (d, 3H), 7.22 (t, 1H). LRMS (APCI): m/z [MH]+236. Microanalysis: Found C, 56.77; H, 6.62; N, 5.06%. $C_{13}H_{17}NO_3$·HCl requires C, 57.46; H, 6.68; N, 5.15%. $[α]_D^{25}$ −6.90° (c=3.1, MeOH).

EXAMPLE 14A (2S,4S)-4-(3-Methoxy-benzyl)-pyrrolidine-2-carboxylic acid mono hydrochloride salt may also be prepared by the method of J. Ezquerra, C. Pedegrel, B. Yrurtagoyena and A. Rubio in *J. Org. Chem.* 1995, 60, 2925-2930.

EXAMPLE 15

(2S,4S)-4-(3-fluoro-phenoxymethyl)-pyrrolidine-2-carboxylic acid

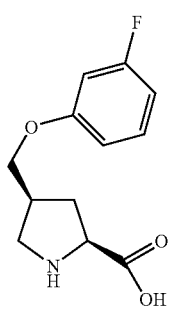

4-(3-fluoro-phenoxymethyl)-pyrroline-1,2-dicarboxylic acid di-tert-butyl ester (Preparation 44, 475 mg, 1.2 mmol) was dissolved in a solution of anhydrous hydrogen chloride in dioxane (4M, 15 ml) and stirred at 50° C. under a nitrogen atmosphere for 1 hour. The solvent was removed under reduced pressure and the resulting semi-solid triturated with ethyl acetate to give a white solid which was recrystallised from ethyl acetate/isopropyl alcohol to give the title compound as a mixture of diastereomers (~5:1 2S,4S:2S,4R) as a white solid hydrochloride salt (90 mg, 35%)

¹H-NMR (400 MHz, CD₃OD): δ=2.04-2.09 (m, 0.8H); 2.33-2.47 (m, 0.4H); 2.65-2.75 (m, 0.8H); 2.88-3.00 (m, 1H); 3.33-3.40 (m, 1H); 3.52-3.60 (m, 0.8H); 3.60-3.68 (0.2H); 3.96-4.04 (m, 1H); 4.04-4.12 (m, 1H); 4.42-4.51 (m, 0.8H); 4.40-4.56 (m, 0.2H); 6.65-6.80 (m, 3H); 7.21-7.30 (m, 1H) LRMS (electrospray): [M+1] 240; [M+23] 262; [M−1] 238.

The following compounds may be prepared by a method analogous to that of Example 15:

EXAMPLE 16

(2S,4S)-4-(2,5-Difluoro-phenoxymethyl)-pyrrolidine-2-carboxylic acid

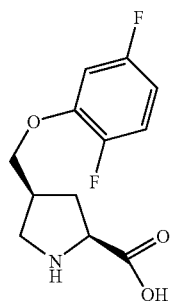

EXAMPLE 17

(2S,4S)-4-(2,3-Difluoro-phenoxymethyl)-pyrrolidine-2-carboxylic acid

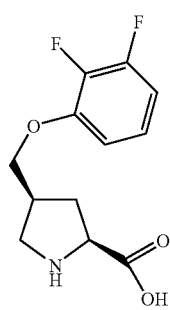

and

EXAMPLE 18

(2S,4S)-4-(3-Methoxy-phenoxymethyl)-pyrrolidine-2-carboxylic acid

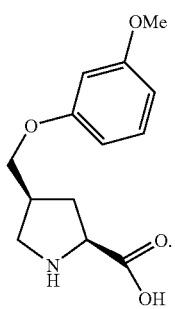

EXAMPLE 19

(2S,4S)-4-(3-chloro-phenoxymethyl)-pyrrolidine-2-carboxylic acid

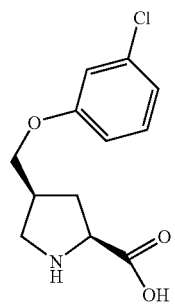

(2S,4S)-4-(3-chloro-phenoxymethyl)-pyrrolidine-1,2-dicarboxylic acid di-tert-butyl ester (Preparation 46, 67 mg, 0.16 mmol) was dissolved in a solution of anhydrous hydrogen chloride in dioxane (4M, 5 ml) and stirred for 18 hours at room temperature. The solvent was removed under reduced pressure and the residue triturated with ethyl acetate to give the title compound as a white solid hydrochloride salt (13 mg, 27%)

¹H-NMR (400 MHz, CD₃OD): δ=2.07-2.18 (m, 1H); 2.63-2.74 (m, 1H); 2.88-3.00 (m, 1H); 3.32-3.40 (m, 1H); 3.52-3.61 (m, 1H); 3.96-4.04 (m, 1H); 4.04-4.10 (m, 1H); 4.42-4.51 (t, 1H); 6.82-6.89 (d, 1H); 6.80-7.00 (m, 2H); 7.20-7.28 (t,1H) LRMS (electrospray): [M+1] 256; [M+23] 278; [M-1] 254

EXAMPLE 20

(2S,4S)-4-(2,3-Dihydro-benzofuran-6-yloxy)-pyrrolidine-2-carboxylic acid

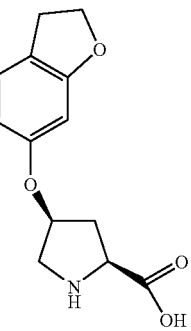

The title compound was made by the method of Example 3 in 100% yield as a pale yellow solid.

¹H-NMR (400 MHz, D₂O): δ=2.35-2.56 (m, 2H); 2.86-3.04 (m, 2H); 3.35-3.65 (m, 2H); 4.10-4.26 (m, 3H); 4.97-5.05 (m, 1H); 6.20-6.36 (m, 2H); 7.02 (d, 1H). LRMS (electrospray): [MH⁺] 250 Microanalysis: Found: C, 54.16; H, 5.78; N, 4.72%. C₁₃H₁₅NO₄.HCl. 0.15H₂O requires C, 54.14; H, 5.70; N, 4.86.

EXAMPLE 21

(2S,4S)-4-(3-Chloro-phenylamino)-pyrrolidine-2-carboxylic acid

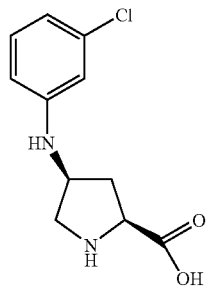

4-(3-Chloro-phenylamino)-pyrrolidine-1,2-dicarboxylic acid 1-tert-butyl ester (Preparation 41, 155 mg, 0.456 mmol) was stirred in 4 M HCl in dioxan (4 ml) at 0° C. for 2 hours. Ether (4 ml) was added and the resultant white hygroscopic solid filtered off and dried in vacuo at 40° C. to give the title compound (90 mg, 60.3%).

$^1$H-NMR (400 MHz, CD$_3$OD): 2.20-2.29(m, 1H); 2.95-3.05 (m, 1H); 3.28-3.29 (m, 2H); 4.22-4.31 (m, 1H); 4.45-4.55 (m, 1H); 4.90 (s, 5H); 6.62 (d, 1H); 6.70-6.75 (m, 2H); 7.13 (t, 1H). LRMS (electrospray): [M−1] 239. Microanalysis: Found: C, 40.37; H, 5.07; N, 8.46%. C$_{11}$H$_{13}$ClN$_2$O$_2$.2HCl. 0.75 H$_2$O requires C, 40.39; H, 5.08; N, 8.56.

Preparation 1

(2S,4R)-4-(Toluene-4-sulfonyloxy)-pyrrolidine-1,2-dicarboxylic acid di-tert-butyl ester

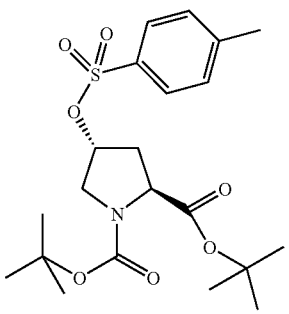

To a solution of (2S,4R)-4-hydroxy-pyrrolidine-1,2-dicarboxylic acid di-tert-butyl ester (CAS Reg. No. 170850-75-6) (1 g, 3.48 mmol) in 20 ml of CH$_2$Cl$_2$ was added pyridine (3.9 ml) and p-toluene sulphonyl chloride (0.7 g, 3.67 mmol) and the mixture stirred at room temperature under a nitrogen atmosphere for 72 hours. The solvent was removed under reduced pressure and the residue dissolved in EtOAc (100 ml) and washed with saturated citric acid solution (50 ml) then water (50 ml). The organic phase was dried (magnesium sulphate), filtered and evaporated under reduced pressure. The residue was purified by column chromatography eluting with ethyl acetate:heptane (3:10) to give the title compound (1.5 g, 98%) as a colourless gum.

$^1$H-NMR (400 MHz, CDCl$_3$) δ=1.39-1.49 (18H, m), 2.01-2.16 (1H, m), 2.33-2.6 (4H, m), 3.50-3.64 (2H, m), 4.20-4.29 (1H, m), 4.96-5.06 (1H, m); 7.31-7.40 (2H, m), 7.65-7.80 (2H, m). LRMS (electrospray): m/z [MH$^+$] 464, [MH$^-$] 440

Preparation 2

(2S,4S)-4-Benzylsulfanyl-pyrrolidine-1,2-dicarboxylic acid di-tert-butyl ester

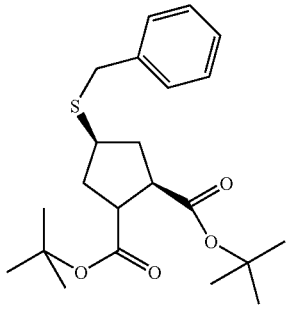

To a solution of Preparation 1 (200 mg, 4.53 mmol) in ethanol (10 ml) under a nitrogen atmosphere was added benzyl mercaptan (0.107 ml, 8.86 mmol) and potassium tert-butoxide (101 mg, 8.86 mmol) and the mixture stirred at room temperature for 18 hours. The solvent was removed under reduced pressure and the residue dissolved in EtOAc (25 ml) and was washed with water (10 ml). The organic phase was dried (magnesium sulphate), filtered and evaporated under reduced pressure. The residue was purified by column chromatography eluting with heptane:ethyl acetate (9:1) to give the title compound (130 mg, 73%) as a colorless oil.

$^1$H-NMR (400 MHz, CDCl$_3$) δ=1.38-1.50 (18H, m), 1.80-1.90 (1H, m), 2.44-2.55 (1H, m), 3.00-3.29 (2H, m), 3.70-3.78 (2H, s), 3.84-3.95 (1H, m), 4.04-4.16 (1H, m), 7.27-7.34 (5H, m). LRMS (electrospray): m/z [MNa$^+$] 416

Preparation 3

(2S,4S)-4-(4-Chloro-benzyloxy)-pyrrolidine-1,2-dicarboxylic acid 1-tert-butyl ester 2-methyl ester

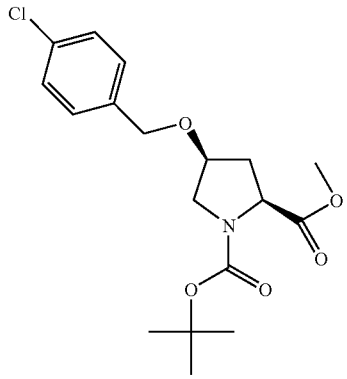

(2S,4S)-4-Hydroxy-pyrrolidine-1,2-dicarboxylic acid 1-tert-butyl ester 2-methyester (CAS Reg. No. 227935-38-8) (300 mg, 1.0 mmol) and 60% sodium hydride mineral oil dispersion (61 mg, 1.1 mmol) were dissolved in anhydrous dimethylformamide (9 ml) at 0° C. under a nitrogen atmosphere. After 10 mins stirring 4-chlorobenzylbromide (265 mg, 1.2 mmol) in CH$_2$Cl$_2$ (1 ml) was added drop wise and the reaction mixture stirred to room temperature for 1 hour. The solvent was removed under reduced pressure and the residue dissolved in ethyl acetate (25 ml), washed with water (2×25 ml), dried (magnesium sulphate), filtered and evaporated under reduced pressure. The residue was purified using flash chromatography eluting with a solvent gradient 4:1 heptane:ethyl acetate, yielding the title compound (170 mg, 40% yield) as an oil.

$^1$H-NMR (400 MHz, CDCl$_3$) δ=1.4-1.5(m, 9H), 2.0-2.45 (m, 2H), 3.5-3.8(m, 5H), 4.05-4.2(s, 1H), 4.25-4.4(m, 1H), 4.4-4.55(m, 2H), 7.3(m, 4H). LCMS (Electrospray): m/z [MNa$^+$] 392.

Preparation 4

(2S,4S)-1-(tert-butoxycarbonyl)-4-[(4-chlorobenzyl)oxy]-pyrrolidine-2-carboxylic acid

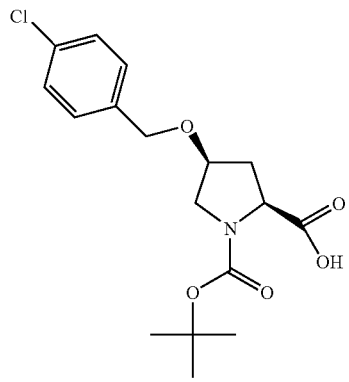

The title compound from Preparation 3 (157 mg, 0.42 mmol) was dissolved in tetrahydrofuran (10 ml). LiOH.H$_2$O (54 mg, 1.3 mmol) was dissolved in water (5 ml). The two solutions were mixed, left stirring at room temperature for two days then evaporated to dryness under reduced pressure. The remaining residue was dissolved in ethyl acetate (25 ml) and washed with saturated citric acid (25 ml). The organic fraction was dried (magnesium sulphate), filtered and evaporated to dryness under reduced pressure. The residue was purified using flash chromatography eluting with a solvent gradient of 20:1 dichloromethane:methanol, yielding the title compound (106 mg, 71% yield) as an oil.

$^1$H-NMR (400 MHz, CDCl$_3$) δ=1.4(m, 9H), 2.9-3.0(m, 1H), 3.4-3.6(m, 2H), 4.2-4.7(m, 5H), 7.2-7.35(m, 4H). LCMS (Electrospray): m/z [M$^-$] 354

Preparation 5

(2S,4S)-4-(4-Bromo-phenylsulfanyl)-pyrrolidine-1,2-dicarboxylic acid 1-tert-butyl ester 2-ethyl ester

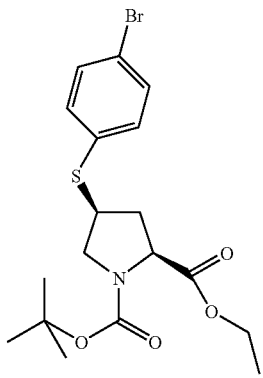

Sodium ethoxide (112 mg, 1.65 mmol) was added slowly to a stirred solution of 4-bromothiophenol (302 mg, 1.65 mmol) in EtOH (6 ml) at room temperature under a nitrogen atmosphere. A solution of (2S,4R)-4-(toluene-4-sulfonyloxy)-pyrrolidine-1,2-dicarboxylic acid 1-tert-butyl ester 2-methyl ester (CAS Reg. No. 88043-21-4) (300 mg, 0.75 mmol) in 1 ml EtOH was added after 30 minutes and the solution was stirred for 48 h. The reaction mixture was poured into 0.5M NaOH (50 ml) and extracted with CH$_2$Cl$_2$ (2×50 ml). The combined organics were dried (magnesium sulphate) and concentrated under vacuum. Flash column chromatography yielded the product as a pink solid (120 mg, 40%).

$^1$H-NMR (400 MHz, CDCl$_3$) δ=1.25 (3H, t), 1.40 (9H, s), 2.00 (1H, s), 2.60 (1H, m), 3.35 (1H, m), 3.60 (1H, m), 3.90 (1H, s), 4.18 (2H, q), 4.22 (1H, m), 7.35 (2H, d), 7.40 (2H, d). LRMS (Electrospray): m/z [MNa$^+$] 454.

Preparation 6

(2S,4S)-4-(phenylsulfanyl)-pyrrolidine-1,2-dicarboxylic acid 1-tert-butyl ester 2-ethyl ester

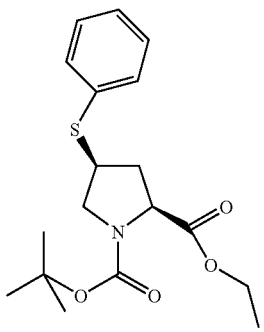

The title compound was made by the method of Preparation 5 in 40% yield as a pink solid.

$^1$H-NMR (400 MHz, CDCl$_3$) δ=1.23 (3H, t), 1.41 (9H, s), 2.00 (1H, m), 2.61 (1H, m), 3.38 (1H, m), 3.62 (1H, m), 3.90-4.03 (1H, m), 4.15-4.35 (3H, m), 7.20-7.50 (5H, m). LRMS (Electrospray): m/z [MNa$^+$] 374.

Preparation 7

(2S,4S)-4-(4-Bromo-phenylsulfanyl)-pyrrolidine-1,2-dicarboxylic acid 1-tert-butyl ester

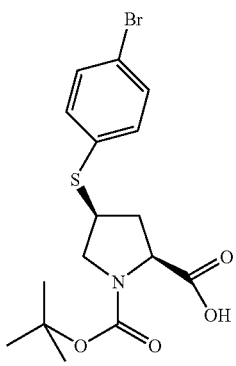

(2S,4S)-4-(4-Bromo-phenylsulfanyl)-pyrrolidine-1,2-dicarboxylic acid 1-tert-butyl ester 2-ethyl ester (Preparation 5, 120 mg, 0.30 mmol) was dissolved in MeOH (6 ml) and 2M sodium hydroxide was added (0.83 ml, 1.66 mmol). The solution was stirred for 14 h, concentrated and added to 0.5M HCl (50 ml). The aqueous was extracted with CH$_2$Cl$_2$ (50 ml) which was dried (magnesium sulphate) and concentrated. Flash column chromatography (eluting first with CH$_2$Cl$_2$ and then with 95% CH$_2$Cl$_2$/MeOH) gave the acid as a clear liquid (130 mg, 48%).

$^1$H-NMR (400 MHz, CDCl$_3$) δ 1.43 (9H, s), 2.4-2.8 (2H, m), 3.35 (1H, m), 3.62 (1H, m), 3.8-4.0 (1H, m), 4.3-4.4 (1H, m), 7.28 (2H, m), 7.41 (2H, m). LRMS (Electrospray): m/z [M$^-$] 400, 402.

Preparation 8

(2S,4S)-4-(Phenylsulfanyl)-pyrrolidine-1,2-dicarboxylic acid 1-tert-butyl ester

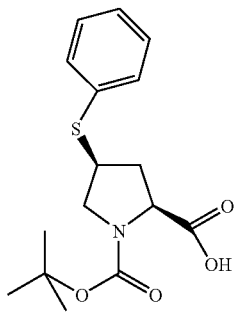

The title compound was made by the method of Preparation 7 from the title compound of Preparation 6 in 83% yield as a clear oil.

$^1$H-NMR (400MHz, CDCl$_3$) δ 1.41 (9H, s), 2.10 (0.5H, m), 2.38 (0.5H, m), 2.50-2.75 (1H, m), 3.36 (1H, m), 3.62 (1H, m), 3.82-4.03 (1H, m), 4.25-4.41 (1H, m), 7.20-7.45 (5H, m). LRMS (Electrospray): m/z [M$^-$] 322.

Preparation 9

4-(2-Fluoro-phenoxy)-pyrrolidine-1,2-dicarboxylic acid 1-tert-butyl ester 2-methyl ester

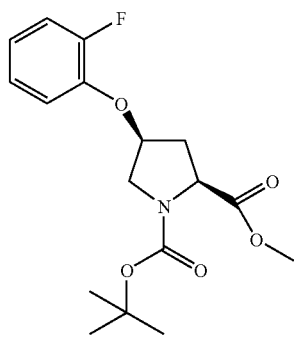

(2S,4R)-4-Hydroxy-pyrrolidine-1,2-dicarboxylic acid 1-tert-butyl ester 2-methyl ester (CAS Reg. No. 74844-91-0) (300 mg, 1.22 mmol) was dissolved in THF (10 ml), and triphenylphosphine (385 mg, 1.47 mmol) and 2-fluorophenol (164.5 mg, 1.47 mmol) were added. The reaction was cooled in ice, DIAD (0.23 ml, 1.2 mmol) added dropwise and the reaction stirred at room temperature overnight. The mixture was concentrated in vacuo, CH$_2$Cl$_2$ (20 ml) added and the solution washed with 2N NaOH (10 ml). The phases were separated and the organic phase washed with saturated brine (10 ml), dried over MgSO$_4$ and evaporated. The residue was dissolved in a minimum of diethylether and pentane added until solution just maintained. After seeding with triphenylphosphine oxide, the solution was cooled in ice and the resultant precipitate filtered. The filtrate was evaporated and the residue purified by flash chromatography on silica (50 g) eluting initially with pentane:diethylether (2:1 by volume), then pentane:diethylether (1:1 by volume) to give the title product (388 mg, 58%) as an impure oil containing diisopropylbicarbamate as an impurity.

$^1$H-NMR (400 MHz, CDCl$_3$): δ=1.45 (d, 9H), 2.35-2.57 (m, 2H),3.65-3.79 (m, 5H), 4.43-4.57 (m, 1H), 4.88-5.02 (m, 1H), 6.81-6.98 (m, 2H), 6.98-7.10 (m, 2H). LRMS (Electrospray): m/z [MNa$^+$] 362

Preparation 10

(2S,4S)-4-(2-Fluoro-phenoxy)-pyrrolidine-1,2-dicarboxyiic acid 1-tert-butyl ester

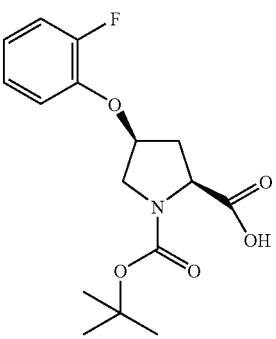

The ester (400 mg, 1.18 mmol) from Preparation 9 was dissolved in THF (4 ml) and LiOH.H$_2$O (106 mg, 3.53 mmol) in water (2 ml) was added. The mixture was stirred at room temperature overnight. After washing with CH$_2$Cl$_2$ (10 ml), the aqueous solution was adjusted to pH 2 with saturated aqueous citric acid and re-extracted with CH$_2$Cl$_2$ (2×10 ml). The combined organic extracts were backwashed with saturated brine, dried over MgSO$_4$, filtered and evaporated to give the title compound as a white solid (383 mg, 49%) containing a small impurity of diisopropylbicarbamate (2%) by NMR.

$^1$H-NMR (400 MHz, CDCl$_3$): δ=1.16-1.70 (m, 9H), 2.20-2.92 (m, 2H), 3.58-3.85 (m, 2H), 4.38-4.63 (m, 1H), 4.83-5.02 (m, 1H), 6.78-7.17 (m, 4H). LRMS (Electrospray): m/z [M−1] 324

Preparation 11

(2S,4S)-4-(4-Chloro-phenoxy)-pyrrolidine-1,2-dicarboxyiic acid 1-tert-butyl ester 2-methyl ester

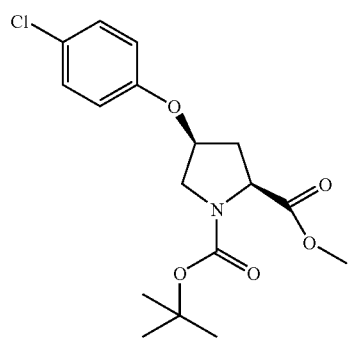

(2S,4R)-4-Hydroxy-pyrrolidine-1,2-dicarboxylic acid 1-tert-butyl ester 2-methyl ester (CAS Reg. No. 74844-91-0)

(1.10 g, 4.08 mmol) was dissolved in THF (25 ml) and 4-chlorophenol (0.78 g, 6.12 mmol) and triphenylphosphine (1.6 g, 6.12 mmol) were added. The solution was cooled in and ice bath and DIAD (0.96 ml, 4.88 mmol) added dropwise. The reaction was stirred at room temperature overnight. After evaporation of the solvent, the residue was dissolved in diethylether (20 ml) and pentane added until solution was only just maintained. The solution was seeded with triphenylphosphine oxide and cooled in ice. The resultant precipitate was filtered and the filtrate evaporated. The residue was purified by flash chromatography on silica (100 g), loading with pentane:diethylether (2:1 by volume) and eluting with pentane : diethylether (1:1 by volume) to give the title compound as a colourless oil (1.35 g, 69%) containing a small impurity of diisopropylbicarbamate (CAS Reg. No.19740-72-8) by NMR.

$^1$H-NMR (400 MHz, CDCl$_3$): δ=1.43 (d, 9H), 2.36-2.57 (m, 2H), 3.61-3.81 (m, 5H), 4.39-4.59 (m, 1H), 4.80-4.90 (m, 1H), 6.64-6.78 (m, 2H), 7.18-7.30 (m, 2H). LRMS (Electrospray): mlz [MNa$^+$] 378

Preparation 12

(2S,4S)-4-(4-Chloro-Dhenoxy)-pyrrolidine-1,2-dicarboxylic acid 1-tert-butyl ester

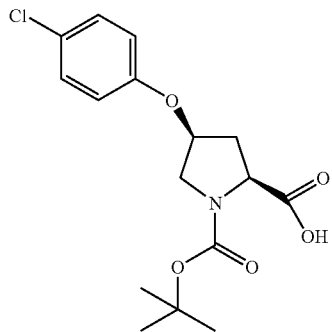

The ester from Preparation 11 was dissolved in THF (30 ml) and a solution of LiOH.H$_2$O (440 mg, 10.56 mmol) in water (15 ml) was added. The reaction was stirred at room temperature overnight, and then the solvent concentrated in vacuo. The residue was partitioned between CH$_2$Cl$_2$ (20 ml) and saturated aqueous citric acid solution (10 ml) and the phases separated. The organic layer was washed with saturated brine (10 ml), dried over MgSO$_4$, and evaporated. The crude product was partially purified by flash chromatography on silica (100 g) eluting initially with CH$_2$Cl$_2$ and then CH$_2$Cl$_2$:MeOH (25:1 by volume) to give material which still contained diisopropylbicarbamate by NMR. Recrystallisation from EtOAc yielded white crystals which were filtered and washed with EtOAc:pentane (1:1) to give the title compound (517 mg, 55%).

$^1$H-NMR (400 MHz, CDCl$_3$): δ=1.23-1.67 (m, 9H), 2.20-2.88 (m, 2H), 3.55-3.81 (m, 2H), 4.40-4.61 (m, 1H), 4.78-4.92 (m, 1H), 6.63-6.84 (m, 2H), 7.11-7.32 (m, 2H) LRMS (Electrospray): m/z [M−1] 340

Preparation 13

(2S,4S)-4-(Isoquinolin-7-yloxy)-pyrrolidine-1,2-dicarboxylicacid di-tert-butyl ester

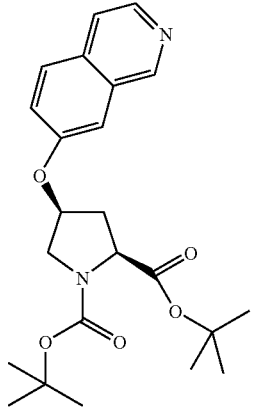

The title compound was synthesised from (2S,4R)-4-hydroxy-pyrrolidine-1,2-dicarboxylic acid di-tert-butyl ester (CAS Reg. No. 170850-75-6) and isoquinolin-7-ol using the same method as preparation 11 and gave the title compound as an oil in 15% yield.

$^1$H-NMR (400 MHz, CDCl$_3$): δ=1.41-1.53 (m, 18H), 2.43-2.63 (m, 2H), 3.68-3.97 (m, 2H), 4.30-4.52 (m, 1H), 4.99-5.06 (m, 1H), 7.08-7.16 (m, 1H), 7.41-7.77 (m, 3H), 8.42 (d, 1H), 9.10-9.18 (m, 1H). LCMS (Electrospray): m/z [MH$^+$] 415

Preparation 14

(2S,4S)-4-(3-Chloro-phenoxy)-pyrrolidine-1,2-dicarboxylic acid 1-tert-butyl ester 2-methyl ester

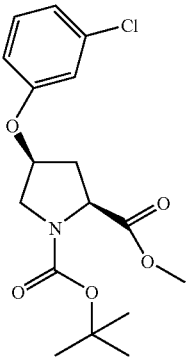

To a stirred solution of (2S,4R)-4-hydroxy-pyrrolidine-1, 2-dicarboxylic acid 1-tert-butyl ester 2-methyl ester (CAS Reg 74844-91-0) (6.1 kg, 24.87 mol), 3-chlorophenol (3.52 kg, 27.39 mol) & triphenylphosphine (7.18 kg, 27.37 mol) in tert-butyl methyl ether (30.5 L) at 0'C. was added diisopropylazodicarboxylate (5.53 kg, 27.35 mol) in tert-butyl methyl ether (15 L) dropwise. The mixture was stirred overnight at 20'C. The reaction was filtered and the liquors washed with 0.5M sodium hydroxide (aq) (2×12.5 L) & water (12.2 L). The tert-butyl methyl ether solvent was replaced with n-heptane (42.7 L) by atmospheric pressure distillation & cooled to crystallise crude product, which was collected by filtration (11.1 kg, 125% contaminated with ca 35% reduced diisopropyl dicarboxylate & triphenylphosphine oxide–corrected yield=86%).

¹H NMR (400 MHz, CDCl₃): δ=1.46, 1.49 (2×s, 9H), 2.47 (2H, m), 3.71 (5H, m), 4.42 (1H, m), 4.42, 4.54 (1H, 2×m), 4.87 (1H, m), 6.68 (1H, m), 6.79 (1H, s), 6.92 (1H, m), 7.18 (1H, m). LRMS (Electrospray): m/z 378 (MNa⁺).

Preparation 15

(2S,4S)-4-(3-Chloro-phenoxy)-pyrrolidine-1,2-dicarboxylic acid 1-tert-butyl ester

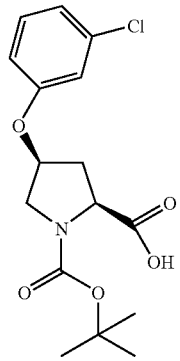

To the products of preparation 14 (11.1 kg, 20.28 mol) in THF (26.6 L) was added a solution of LiOH.H₂O (4.86 kg, 115.4 mol) in water (55.5 L). The mixture was stirred overnight at 25° C. The THF was removed by distillation & the resultant aqueous solution extracted with dichloromethane (33.3 L & 16.7 L). The combined dichloromethane layers were extracted with water (33 L & 16.7 L). The combined aqueous phases were adjusted to pH 3-3.5 with 1M hydrochloric acid(aq) & extracted with dichloromethane (2×22.2 L). The combined dichloromethane phases were replaced with toluene (33.3 L), which was cooled to crystalline the product, which was collected by filtration (6.1 kg, 98%).

¹H NMR (400 MHz, CDCl₃): δ=1.42, 1.48 (2×s, 9H), 2.30-2.70 (m, 2H), 3.60-3.80 (m, 2H), 4.40-4.60 (m, 1H), 4.86 (m, 1H), 6.71 (m, 1H), 6.82 (m, 1H), 6.94 (m, 1H), 7.16 (m, 1H). LRMS (Electrospray): m/z [MNa⁺] 364, 340 [M−1] 340.

Preparation 16

(2S,4S)-4-Benzyloxy-pyrrolidine-1,2-dicarboxylic acid 1-tert-butyl ester 2-methyl ester

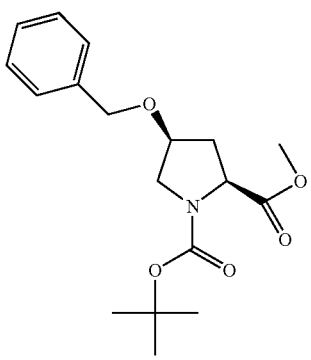

(2S,4S)-4-Hydroxy-pyrrolidine-1,2-dicarboxylic acid 1-tert-butyl ester 2-methyl ester (CAS Reg. No. 227935-38-8)(300 mg, 1.2 mmol) and 60% sodium hydride mineral oil dispersion (61 mg, 1.5 mmol) were dissolved in anhydrous dimethylformamide (9 ml) at 0° C. under a nitrogen atmosphere. After 10 mins stirring benzylbromide (0.153 ml, 1.3 mmol) in CH₂Cl₂ (1 ml) was added drop wise and the reaction mixture stirred to room temperature for 1 hour. The solvent was removed under reduced pressure and the residue dissolved in ethyl acetate (25 ml), washed with water (2×25 ml), dried (magnesium sulphate), filtered and evaporated under reduced pressure. The residue was purified using flash chromatography eluting with a solvent gradient 4:1 heptane:ethyl acetate, yielding the title compound (167 mg, 42% yield) as an oil.

¹H-NMR (400MHz, CDCl₃) δ=1.2-1.6(m, 12H), 2.2-2.45 (m, 1H), 3.4-3.8 (m, 4H), 4.05-4.2 (m, 1H), 4.3-4.5 (m, 2H), 7.15-7.4 (m, 5H). LCMS (Electrospray): m/z [MNa⁺] 358.

Preparation 17

(2 S,4S)-1-(tert-Butoxycarbonyl)-4-(benzyloxy)-pyrrolidine-2-carboxylic acid

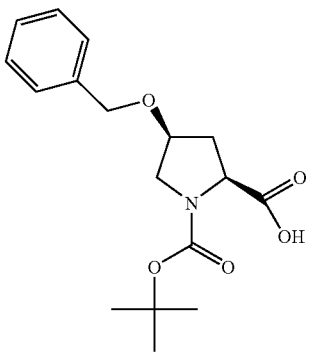

The title compound from Preparation 16 (167 mg, 0.5 mmol) was dissolved in tetrahydrofuran (10 ml). LiOH.H₂O (63 mg, 1.5 mmol) was dissolved in water (5 ml). The two solutions were mixed, left stirring at room temperature for two days then evaporated to dryness under reduced pressure. The remaining residue was dissolved in ethyl acetate (25 ml) and washed with saturated citric acid (25 ml). The organic fraction was dried (magnesium sulphate), filtered and evaporated to dryness under reduced pressure. The crude compound (150 mg, 94% yield) was taken on to the next stage (Example 9) as an oil.

LCMS (Electrospray): m/z [M⁻] 320, [MNa⁺] 344.

Preparation 18

(2S,4S)-4-(2,3-Dihydro-benzofuran-6-yloxy)-pyrrolidine-1,2-dicarboxylic acid 1-tert-butyl ester 2-methyl ester

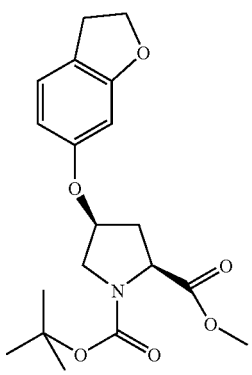

The title compound was prepared from (2S,4R)-4-hydroxy-pyrrolidine-1,2-dicarboxylic acid 1-tert-butyl-ester 2-methyl ester and 2,3-dihydro-benzofuran-6-ol by the method of Preparation 14 in 41.6% yield as a white solid.

¹H-NMR (400 MHz, CDCl₃): δ=1.43 (d, 9H); 2.36-2.50 (m, 2H); 3.03-3.17 (m, 2H); 3.59-3.80 (m, 5H); 4.15-4.41 (m,

3H); 4.78-4.83 (m, 1H); 6.21-6.32 (m, 2H); 6.98-7.02 M, 1H). LRMS (electrospray): [MNa+] 386

Preparation 19

(2S,4S)-4-(2,3-Dihydro-benzofuran-6-yloxy)-pyrrolidine-1,2-dicarboxylic acid 1-tert-butyl ester

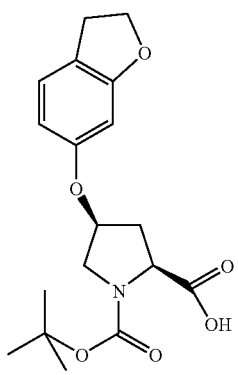

The title compound was made from 4-(2,3-dihydro-benzofuran-6-yloxy)-pyrrolidine-1,2-dicarboxylic acid 1-tert-butyl ester 2-methyl ester by the method of Preparation 15 in 78% yield as a white solid.
$^1$H-NMR (400 MHz, CDCl$_3$): δ=1.38-1.58 (m, 9H); 2.21-2.83(m, 2H); 3.02-3.18 (m, 2H); 3.59-3.82 (m, 2H); 4.38-4.60 (m, 3H); 4.80-4.90 (m, 1H); 6.22-6.42 (m, 2H); 6.97-7.10(m, 1H). LRMS (electrospray): [M−1] 348

Preparation 20

4-(3-Fluoro-benzylidene)-pyrrolidine-1,2-dicarboxylic acid-1-tert butyl ester 2-methyl ester

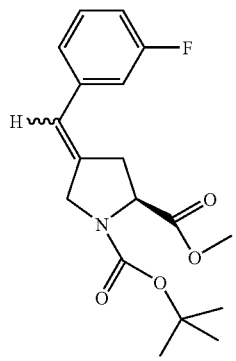

To a solution of m-Fluorobenzyl triphenylphosphonium[2] bromide (8.08 g, 0.018 mmol) in anhydrous dichloromethane (200 ml), was added potassium t-butoxide (1M in THF, 17.2 ml, 0.017 mmol) dropwise at room temperature and stirred for 1 h. The mixture was cooled to 0° C. and to this a solution of the (2S) 4-oxo-pyrrolidine-1,2-dicarboxylic acid 1-tert butyl ester 2-methyl ester[3] (3.8 g, 0.016 mmol) in dichloromethane (20 ml) was added dropwise. The mixture was warmed to room temperature and stirred for 18 hours. The reaction was quenched with saturated ammonium chloride (100 ml), the aqueous extracted with dichloromethane (2×100 ml) and the combined organics dried over magnesium sulfate. The solvent removed by evaporation under reduced pressure. The residue was purified by flash chromatography on silica gel eluting with a solvent gradient of heptane:ethyl acetate (4:1) to give the title compound (3.48 g, 67%) as a colourless oil.
$^1$H-NMR (400 MHz, CD$_3$OD) (mixture of geometric isomers, cis and trans): δ=1.44 (s, 10H), 1.50 (s, 8H), 2.79-2.94 (m, 2H), 3.20-3.37 (m, 2H), 3.66 (d, 3H), 3.72 (d, 3H), 4.20-4.38 (m, 4H), 4.42-4.48 (m, 1H), 4.52-4.60 (m, 1H), 6.42-6.51 (m, 2H), 6.89-7.10 (m, 6H), 7.30-7.40 (m, 2H). LRMS (APCI): m/z [(M+H)-Boc]$^+$236. Microanalysis: Found: C, 64.46; H, 6.77; N, 4.07%. C$_{18}$H$_{22}$ FNO$_4$. requires C, 64.46; H, 6.61; N, 4.18%.

2. K. Rafizadeh and K. Yates; *J.Org. Chem.* 1984, 49, 9,1500-1506.

3. *Org. Lett*, 2001, 3041-3043.

Preparations 21-24

The compounds of the following tabulated examples of the general formula:

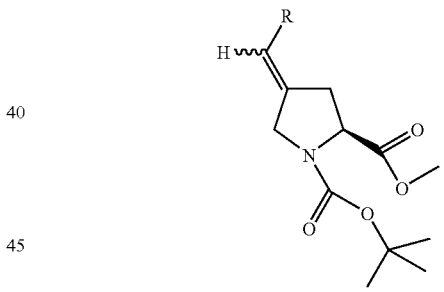

were prepared by a method analogous to that of Preparation 20 using the appropriate phosphonium bromide salt and (2S) 4-oxo-pyrrolidine-1,2-dicarboxylic acid 1-tert butyl ester 2-methyl ester[3]

| Prep. no. | R | LRMS (APCI) m/z = [ ]$^+$ | Analytical data |
|---|---|---|---|
| 21 | ![2,5-difluorophenyl] | 354 [MH] | $^1$H-NMR(400MHz, CD$_3$OD): (mixture of geometric isomers cis and trans)δ = 1.45(d, 9H), 2.78-2.88(m, 1H), 3.20-3.32(m, 1H), 3.70(d, 3H), 4.15-4.31(m, 2H), 4.50(dt, 1H), 6.51(s, 1H), 6.98-7.13(m, 3H). |

-continued

| Prep. no. | R | LRMS (APCI) m/z = [ ]+ | Analytical data |
|---|---|---|---|
| 22 | 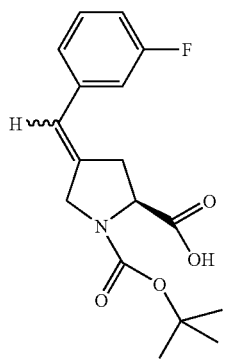 (difluorophenyl, omitted—see image) | 254 [(M − H)−Boc] | Microanalysis: Found: C, 61.25; H, 6.16; N, 3.89%. $C_{18}H_{21}F_2NO_4$. requires C, 61.18; H, 5.99; N, 3.96%; $[\alpha]_D^{25}$ −5.52° (c = 2.68 in methanol) |
| 23 | (2,5-dichlorophenyl) | 286 [M-Boc] | $^1$H-NMR(400 MHz, CD$_3$OD)(mixture of geometric isomers, cis and trans): δ = 1.44(2 × s, 5H), 1.50(2 × s, 4H), 2.70-2.92(m, 1H), 3.20-3.40(m, 1H), 3.69(d, 1.5H), 3.72(d, 1.5H), 4.08-4.20(m, 0.5H), 4.23-4.29 (m, 1.5H), 4.44-4.59(m, 0.5H), 4.51-4.57(m, 0.5H), 6.55-6.64(brm, 1H), 7.23-7.30(m, 1.5H), 7.34(d, 0.5H), 7.37-7.42(m, 1H). Microanalysis: Found: C, 56.63; H, 5.74; N, 3.58%. $C_{18}H_{21}C_{12}NO_4.0.05$ heptane. requires C, 56.33; H, 5.62; N, 3.58%; $[\alpha]_D^{25}$ = 8.70° (c = 3.08 in methanol) |
| 24 | (3-methoxyphenyl) | 348 [MH] | $^1$H-NMR(400MHz, CD$_3$OD):(mixture of geometric isomers, cis and trans) δ = 1.45(d, 9H), 2.77-2.91 (m, 1H), 3.23-3.30(m, 1H), 3.70(dd(3H), 3.78(s, 3H), 4.19-4.30(m, 2H), 4.49(dt, 1H), 6.42-6.48(m, 1H, 6.75-6.85(m, 3H), 7.22-7.28(m, 1H). Microanalysis: Found: C, 68.66; H, 7.48; N, 4.12%. $C_{19}H_{25}NO_5$ requires C, 68.86; H, 7.60; N, 4.23% |

Preparation 25

4-(3-Fluoro-benzylidene)-pyrrolidine-1,2-dicarboxylic acid-1-tert butyl ester

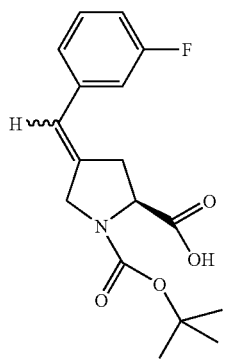

To a stirred solution of 4-(3-Fluoro-benzylidene)-pyrrolidine-1,2-dicarboxylic acid 1-terf butyl ester 2-methyl ester (3.23 g, 9.63 mmol) in tetrahydrofuran (150 ml), was added 1M lithium hydroxide monohydrate (1.21 g, 28.9 mmol) in water (50 ml). The mixture was stirred at room temperature for 3 days. Tetrahydrofuran was removed by evaporation under reduced pressure, the residue diluted with water (30 ml) and acidified to pH 2.0-3.0 using 1M hydrochloric acid. The aqueous was extracted with diethyl ether (3×100 ml) and the combined organics dried over magnesium sulfate. The solvent was removed by evaporation under reduced pressure to give the title compound (2.37 g, 77%) as a white foam.

$^1$H-NMR (400 MHz, CD$_3$OD) (mixture of geometric isomers, cis and trans): δ=1.44 (s, 5H), 1.50 (s, 4H), 2.80-2.96 (m, 1H), 3.20-3.38 (m, 1H), 4.24-4.34 (m, 2H), 4.45-4.45 (m, 0.5H), 4.46-4.58 (m, 0.5H), 6.43-6.54 (m, 1H), 6.90-7.05 (m, 3H), 7.30-7.40 (m, 1H). LRMS (APCI): m/z [M–H]$^+$320. Microanalysis: Found: C, 63.10; H, 6.53; N, 4.05%. $C_{17}H_{20}NO_4F$ requires C, 63.54; H, 6.27; N, 4.36%.

Preparations 26-29

The compounds of the following tabulated examples of the general formula:

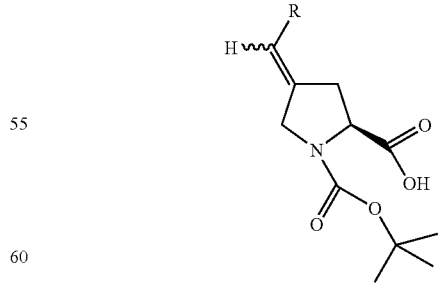

were prepared by a method analogous to that of Preparation 25 using the appropriate starting ester.

| Prep. no. | R | LRMS (APCI) m/z = [ ]+ | Analytical data |
|---|---|---|---|
| 26 | ![2,5-difluorophenyl] | 677 [2M – H] | ¹H-NMR(400MHz, CD₃OD): (mixture of geometric isomers, cis and trans): δ=1.44(d, 9H), 2.75-2.92 (m, 1H), 3.18-3.32(m, 1H), 4.14-4.31(m, 2H), 4.40-4.55(m, 1H), 6.53(s, 1H), 6.95-7.14(m, 3H). |
| 27 | ![2,3-difluorophenyl] | 338 [M – H] | ¹H-NMR(400 MHz, CD₃OD) (mixture of geometric isomers, cis and trans): δ = 1.42-1.56(m, 9H), 2.78-2.92(m, 1H), 3.20-3.36(m, 1H), 4.05-4.52 (m, 2H), 4.40-4.56(m, 1H), 6.54-6.60(brs, 1H), 7.00-7.20(m, 3H). Microanalysis: Found: C, 59.61; H, 5.80; N, 3.97%. C₁₇H₁₉F₂NO₄. requires C, 60.17; H, 5.64; N, 4.13%. [α]$_D^{25}$ –3.64° (c = 2.58 in methanol) |
| 28 | ![2,5-dichlorophenyl] | 370 [M – 2H] | ¹H-NMR(400 MHz, CD₃OD) (mixture of geometric isomers, cis and trans): δ = 1.48(2×s, 5H), 1.52 (2×s, 4H), 2.75-2.80(m, 0.5H), 2.85-2.95(m, 0.5H), 3.20-3.33(m, 1H), 4.10-4.20(m, 0.5H), 4.24-4.34(m, 1.5H), 4.40-4.54(m, 1H), 6.55-6.65 (brs, 1H), 7.24-7.28(m, 1.5H), 7.38(d, 0.5H), 7.40 (d, 1H). Microanalysis: Found: C, 54.69; H, 5.29; N, 3.64%. C₁₇H₁₉Cl₂NO₄. requires C, 54.85; H, 5.14; N, 3.76%. |
| 29 | ![3-methoxyphenyl] | 332 [M – H] | ¹H-NMR(400MHz, CD₃OD): (mixture of geometric isomers, cis and trans): δ = 1.44(d, 9H), 2.79-2.95 (m, 1H), 3.19-3.30(m, 1H), 3.79(s, 3H), 4.23-4.39 (m, 2H), 4.40-4.49(m, 1H), 6.43-6.45(m, 1H), 6.73-6.84(m, 3H), 7.22-7.29(m, 1H). |

Preparation 30

4-(3-Fluoro-benzylidene)-pyrrolidine-1,2-dicarboxylic acid 1-tert-butyl ester 2-(2-isopropyl-5-methyl-cyclohexyl)ester

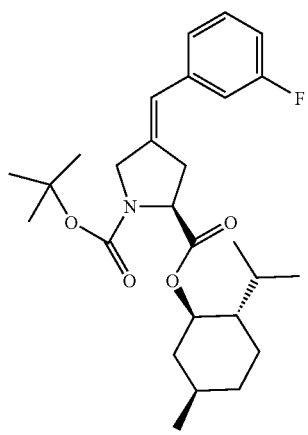

To a solution of 4-(3-Fluoro-benzylidene)-pyrrolidine-1,2-dicarboxylic acid 1-tert-butyl ester (2.68 g, 8.35 mmol), 1R,2S,5R(–) menthol (1.31 g, 8.35 mmol) was added followed by dimethylaminopyridine (1.02 g, 8.35 mmol). The mixture was cooled to 0° C. and dicyclohexylcarbodiimide (1.89 g, 9.19 mmol) in dichloromethane (10 ml) was added in one portion. The mixture was warmed to room temperature stirred for 18 h. The mixture was filtered and the filtrate was washed with 1N hydrochloric acid (30 ml), sat. sodium hydrogen carbonate (30 ml) and water (30 ml). The organics were dried over magnesium sulphate and the solvent was removed by evaporation under reduced pressure. Purification by flashmaster column chromatography eluting with heptane: ethyl acetate (12:1) yielded the title compound (1.20 g, 31%) as a colourless oil.

¹H-NMR (400 MHz, CD₃OD): δ=0.55 (t, 2H), 0.69 (t, 2H), 0.80-0.93 (m, 8H), 0.95-1.05 (m, 1H), 1.20-1.35 (m, 2H), 1.44 (d, 9H), 1.60-2.00 (m, 3H), 2.73-2.90 (m, 1H), 4.03-4.68 (m, 4H), 6.43-6.52 (m, 1H), 6.93-7.11 (m, 3H), 7.33-7.40 (m, 1H). LRMS (APCI): m/z [MH]⁺ 460.

Preparations 31-34

The compounds of the following tabulated examples of the general formula:

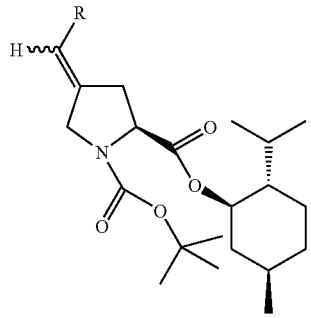

were prepared by a method analogous to that of Preparation 30 using the appropriate starting acid.

| Prep. no. | R | LRMS (APCI) m/z = | Analytical data |
|---|---|---|---|
| 31 | (2,5-difluorophenyl) | 378 [MH-Boc] | Microanalysis: Found C, 67.31; H, 7.88; N, 2.89%. $C_{27}H_{37}F_2NO_2$ requires C, 67.90; H, 7.81; N, 2.93%. |
| 32 | (2,3-difluorophenyl) | 478 [MH] | Microanalysis: Found: C, 68.64; H, 8.29; N, 2.7%. $C_{27}H_{37}F_2NO_4 \cdot 0.13$ heptane requires C, 68.33; H, 8.03; N, 2.85%; $[\alpha]_D^{25}$ −35.57° (c = 3.2 in methanol) |
| 33 | (2,5-dichlorophenyl) | 510 [MH] | Microanalysis: Found C, 63.75; H, 7.39; N, 2.73%. $C_{27}H_{37}Cl_2NO_4$ requires C, 63.53; H, 7.31; N, 2.74%. |
| 34 | (3-methoxyphenyl) | 372 [MH] | Microanalysis: Found C, 70.60; H, 8.72; N, 2.99%. $C_{28}H_{41}NO_5$ requires C, 71.31; H, 8.76; N, 2.97%. $[\alpha]_D^{25}$ −47.24° (c = 1.66, MeOH) |

Preparation 35

4-(3-Fluoro-benzyl)-pyrrolidine-1,2-dicarboxylic acid 1-tert-butyl ester 2-(2-isopropyl-5-methyl-cyclohexyl)ester

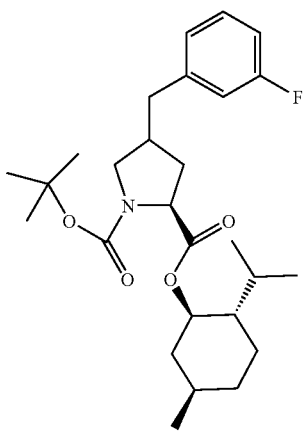

4-(3-Fluoro-benzylidene)-pyrrolidine-1,2-dicarboxylic acid 1-tert-butyl ester 2-(2-isopropyl-5-methyl-cyclohexyl) ester (1.20 g, 2.61 mmol) was dissolved in ethyl acetate: toluene (1:1, 12 ml). The solution was submitted to hydrogenation on platinum oxide (120 mg, 10% by weight) at 25° C. and 15 psi for 1 hour. The reaction mixture was filtered through arbocel and the filtrate reduced under pressure. The residue was purified by flashmaster chromatography eluting with heptane:ethyl actetate (15:1) to yield the title compound as a colourless oil (1.11 g, 91%).

$^1$H-NMR (400 MHz, $CD_3OD$): δ=0.72-1.37 (m, 13H), 1.44 (d, 9H), 1.43-1.75 (m, 4H), 1.87-2.01 (m, 2H), 2.31-2.58 (m, 2H), 2.83 (d, 2H), 3.07 (t, 1H), 3.50-3.65 (m, 1H), 4.13-4.30 (dt, 1H), 4.71 (td, 1H), 6.90 (d, 2H), 7.00 (d, 1H), 7.30 (q, 1H). LRMS (APCI): m/z [MH−BOC]$^+$ 362.

Preparations 36-39

The compounds of the following tabulated examples of the general formula:

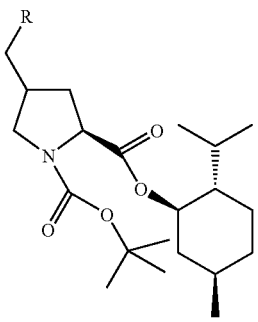

were prepared by a method analogous to that of Preparation 35 using the appropriate starting alkenic menthol ester.

| Prep. no. | R | LRMS (APCI) m/z = | Analytical data (mixture of diastereoisomers cis (major) and trans): |
|---|---|---|---|
| 36 | (2,5-difluorophenyl) | 380 [MH] | Microanalysis: Found C, 67.22; H, 8.24; N, 2.95%. $C_{27}H_{39}F_2NO_4$ requires C, 67.62; H, 8.20; N, 2.92%. |
| 37 | (2,3-difluorophenyl) | 480 [MH] | Microanalysis: Found: C, 67.74; H, 8.30; N, 2.90%. $C_{27}H_{39}F_2NO_4$ requires C, 67.62; H, 8.20; N, 2.92%; $[\alpha]_D^{25}$ −71.92° (c = 3.26 in methanol) |
| 38[1] | (cyclohexyl) | 350 [MH-Boc] | |
| 39 | (3-methoxyphenyl) | 374 [MH] | Microanalysis: Found C, 71.02; H, 9.27; N, 2.97%. $C_{28}H_{43}NO_5$ requires C, 71.00; H, 9.15; N, 2.96%. $[\alpha]_D^{25}$ −2.76° (c = 5.3 in methanol) |

Footnotes
[1]Hydrogenation of the title compound of Preparation 33 was carried out using rhodium on alumina (5%) (44 mg, 10% by weight) at 50° C., 70 psi for 24 h.

Preparation 40

(2S,4S)-4-(3-Chloro-phenylamino)-pyrrolidine-1,2-dicarboxylic acid 1-tert-butyl ester 2-methyl ester

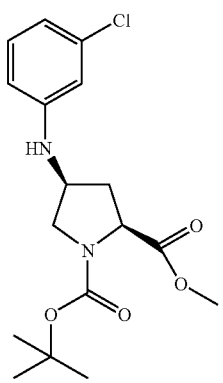

4-Oxo-pyrrolidine-1,2-dicarboxylic acid 1-tert-butyl ester 2-methyl ester (364.5 mg, 1.5 mmol) and 3-chloroaniline (191 mg, 1.5 mmol) were dissolved in DCM (10 ml). To this solution was added sodium triacetoxyborohydride (413 mg, 1.95 mmol) and acetic acid (0.085 ml, 1.5 mmol), and the reaction stirred at room temperature overnight. The reaction mixture was washed with 2N NaOH (5 ml), saturated brine (5 ml), dried over $MgSO_4$ and evaporated. The residue was purified by flash chromatography on silica eluting with DCM to give the title compound as a colourless oil (215 mg, 40%).
$^1$H-NMR (400 MHz, $CDCl_3$): δ=1.42 (d, 9H); 2.04-2.17 (m, 1H); 2.39-2.55 (m, 1H); 3.48-3.61 (m, 1H); 3.63-3.79(m, 4H); 4.02-4.15 (m, 1H); 4.25-4.41 (m, 1H); 6.42-6.51 (m, 1H); 6.55-6.61 (m, 1H); 6.65-6.75 (m, 1H); 7.01-7.11 (m, 1H). LRMS (electrospray): [MNa$^+$] 377.

Preparation 41

(2S,4S)-4-(3-Chloro-phenylamino)-pyrrolidine-1,2-dicarboxylic acid 1-tert-butyl ester

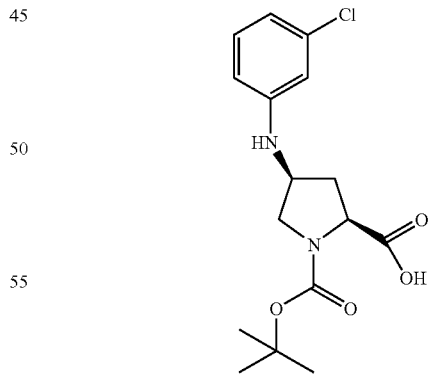

To a solution of the (2S,4S)-4-(3-chloro-phenylamino)-pyrrolidine-1,2-dicarboxylic acid 1-tert-butyl ester 2-methyl ester (200 mg, 0.58 mmol) in THF (2 ml) was added a solution of LiOH.H$_2$O (73 mg 1.74 mmol), and the reaction stirred at room temperature overnight. The solvent was concentrated in vacuo and the residual aqueous solution washed with DCM (2 ml). The aqueous was then adjusted to pH 5 with saturated aqueous citric acid and re-extracted with DCM (2×10 ml).

These combined extracts were dried over MgSO₄ and evaporated to give the title compound as a white foam (168 mg, 88%)

¹H-NMR (400 MHz, CDCl₃): δ=1.18-1.69 (m, 9H); 2.11-2.45 (m, 1H); 2.53-2.61 (m, 1H); 3.44-3.62 (m, 2H); 4.04-4.11 (m, 1H); 4.48-4.53 (m, 1H); 6.38-6.61 (m, 2H);6.65-6.74 (m, 1H); 7.04-7.15 (m, 1H). LRMS (electrospray): [M−1] 339

Preparation 42

4-hydroxymethyl-pyrrolidine-1,2-dicarboxylic acid di-tert-butyl ester

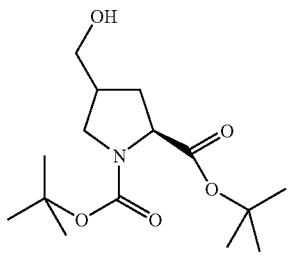

To a solution of 2-methyl-2-butene (2M in tetrahydrofuran, 30 ml, 60 mmol) in anhydrous tetrahydrofuran (40 ml) at 0° C. under a nitrogen atmosphere was added borane-tetrahydrofuran complex (1M in tetrahydrofuran, 30 ml, 30 mmol) dropwise over 10 minutes and allowed to stir for 2 hours. The reaction mixture was cooled to −20° C. and a solution of 4-methylene-pyrrolidine-1,2-dicarboxylic acid di-tert-butyl ester (2.84 g, 10 mmol) (CAS reg 163 190-46-3) in tetrahydrofuran (20 ml) was added dropwise and stirred to room temperature over 18 hours. Water (40 ml) was added cautiously followed by sodium hydroxide (0.5M, 20 ml) then hydrogen peroxide (27.5% w/w in water, 10 ml) and stirred at room temperature for 2 hours. The organic solvent was removed under reduced pressure and the aqueous extracted with ethyl acetate (2×60 ml). The combined extracts were dried (MgSO₄), filtered and evaporated under reduced pressure. The residue was purified by chromatography on silica gel, eluting with 40% ethyl acetate/heptane to give the title compound as a mixture of diastereomers (~5:1 2S,4S:2S,4R) as a colourless oil (1.25 g, 41%)

¹H-NMR (400 MHz, CD₃OD): δ=1.39-1.49 (m, 18H); 1.63-1.75 (m, 0.8H); 1.96-2.07 (m, 0.4H); 2.32-2.47 (m, 1.8H); 3.11-3.20 (m, 1H); 3.46-3.53 (m, 2H); 3.53-360 (m, 0.2H); 3.60-3.68 (m, 0.8H); 4.09-4.2 (m, 1H) LRMS (electrospray): [M+23] 324; [M−1] 300

Preparation 43

4-(3-fluoro-phenoxymethyl)-pyrroline-1,2-dicarboxylic acid di-tert-butyl ester

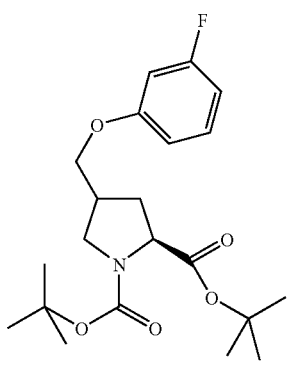

To a solution of 4-hydroxymethyl-pyrrolidine-1,2-dicarboxylic acid di-tert-butyl ester (Preparation 42, 500 mg, 1.66 mmol), triphenylphosphine (653 mg, 2.49 mmol) and 3-fluorophenol (0.23 ml, 2.49 mmol) in tetrahydrofuran (30 ml) at 0° C. under a nitrogen atmosphere was added diisopropylazodicarboxylate (0.49 ml, 2.49 mmol) dropwise over 5 minutes and stirred to room temperature over 72 hours. Solvent was removed under reduced pressure and the residue purified by chromatography on silica gel, eluting with 10-15% ethyl acetate/heptane to give the title compound as a mixture of diastereomers (~5:1 2S,4S:2S,4R) as a colourless oil (370 mg, 51%)

¹H-NMR (400 MHz, CD₃OD): δ=1.39-1.49 (m, 18H); 1.81-1.95 (m, 0.8H); 2.09-2.20 (m, 0.4H); 2.44-2.59 (m, 0.8H); 2.65-2.80 (m, 1H); 3.22-3.33 (m, 1H); 3.65-3.75 (m, 1H); 3.91-4.00 (m, 1.8H); 4.00-4.07 (m, 0.2H); 4.14-4.26 (m, 1H); 6.60-6.74 (m, 3H); 7.20-7.28 (m, 1H) LRMS (electrospray): [M+23] 418

Preparation 44

(2S,4S)-Pyrrolidine-1,2,4-tricarboxylic acid 1,2-di-tert-butyl ester

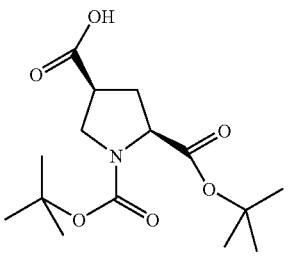

To a mixture of 4-phenyl-pyrrolidine-1,2-dicarboxylic acid di-tert-butyl ester (CAS Reg. No. 344 286-69-7)[5] (0.78 g, 2.24 mmol) and sodium periodate (5.77 g, 27 mmol) stirring at 0° C. under a nitrogen atmosphere in ethyl acetate (5.5 ml), acetonitrile (5.5 ml) and water (8.5 ml) was added ruthenium trichloride (10 mg, 0.05 mmol) and stirred to room temperature over 18 hours. Diethyl ether (20 ml) was added and stirred for a further 1 hr. 1M hydrochloric acid (5 ml) was added and the mixture extracted with ethyl acetate (3×30 ml). Organic extracts were combined, dried (MgSO₄), filtered and evaporated under reduced pressure. The residue was purified by chromatography on silica gel, eluting with 50:50:1 ethyl acetate:heptane:glacial acetic acid to give the title compound as a colourless gum (501 mg, 78%)

¹H-NMR (400 MHz, CDCl₃): δ=1.40-1.49 (m, 18H); 2.26-2.40 (m, 1H); 2.42-2.56 (m, 1H); 3.02-3.12 (m, 1H); 3.65-3.80 (m, 1.4H) & 3.80-3.88 (m, 0.6H) [rotamers]; 4.09-4.20 (m, 0.7H) & 4.20-4.26 (m, 0.3H) [rotamers] LRMS (electrospray): [M−1] 314

[5] J. Org. Chem., 2001, 3593-3596

Preparation 45

(2S,4S)-4-hydroxymethyl-pyrrolidine-1,2-dicarboxylic acid di-tert-butyl ester

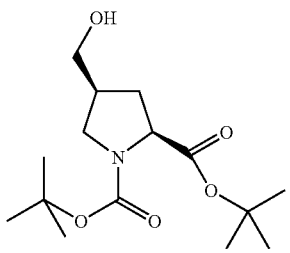

To a solution of pyrrolidine-1,2,4-tricarboxylic acid 1,2-di-tert-butyl ester (Preparation 44, 501 mg, 1.59 mmol) in anhydrous tetrahydrofuran (10 ml) at 0° C. under a nitrogen atmosphere was added borane-tetrahydrofuran complex (1M in tetrahydrofuran, 3.16 ml, 3.18 mmol) dropwise and allowed to stir to room temperature over 18 hours. The solvent was removed under reduced pressure and the residue dissolved in ethyl acetate (10 ml) and washed with 1M hydrochloric acid (10 ml), saturated sodium hydrogen carbonate (10 ml) and then dried (MgSO$_4$), filtered and evaporated under reduced presssure to give the title compound as a colourless gum (single diastereonier 132 mg, 27%)

$^1$H-NMR (400 MHz, CDCl$_3$): δ=1.40-1.47 (m, 18H); 1.59-1.80 (m, 1H); 1.80-2.00 (m, 1H); 2.31-2.46 (m, 2H); 3.14-3.21 (m, 1H); 3.54-3.65 (m, 2H); 3.65-3.74 (m, 1H); 4.10-4.20 (m, 1H).

Preparation 46

(2S,4S)-4-(3-chloro-phenoxymethyl)-pyrrolidine-1, 2-dicarboxylic acid di-tert-butyl ester

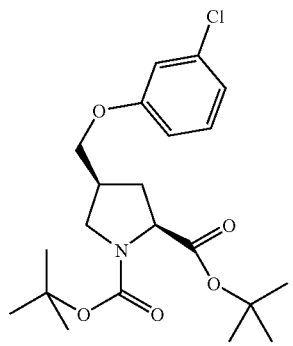

To a solution of 4-hydroxymethyl-pyrrolidine-1,2-dicarboxylic acid di-tert-butyl ester (Preparation 45, 132 mg, 0.44 mmol), triphenylphosphine (172 mg, 0.66 mmol) and 3-chlorophenol (0.069 ml, 0.66 mmol) in tetrahydrofuran (5 ml) at 0° C. under a nitrogen atmosphere was added diisopropylazodicarboxylate (0.129 ml; 0.66 mmol) dropwise and allowed to stir to room temperature over 18 hours. The solvent was removed under reduced pressure and the residue purified by chromatography on silica gel, eluting with 10% ethyl acetate/heptane to give the title compound as a colourless gum (66 mg, 37%).

$^1$H-NMR (400 MHz, CDCl$_3$): δ=1.40-1.56 (m, 18H); 1.80-1.91 (m, 1H); 2.40-2.54 (m, 1H); 2.61-2.70 (m, 1H); 3.24-3.33 (m, 1H); 3.67-3.74 (m, 0.3H) & 3.74-3.81 (m, 0.7H) [rotamers]; 3.84-3.96 (m, 2H); 4.12-4.20 (m, 0.7H) & 4.20-4.26 (m, 0.3H) [rotamers]; 6.67-6.75 (m, 1H); 6.82-6.86 (m, 1H); 6.86-6.93 (m, 1H); 7.10-7.19 (m, 1H) LRMS (electrospray): [M+23] 434

Pharmaceutical Composition Examples

In the following Examples, the term 'active compound' or 'active ingredient' refers to a compound of formula (I) or a pharmaceutically acceptable salt, solvate, polymorph or prodrug thereof, according to the present invention.

(i) Tablet Compositions

The following compositions A and B can be prepared by wet granulation of ingredients (a) to (c) and (a) to (d) with a solution of povidone, followed by addition of the magnesium stearate and compression.

|  | mg/tablet | mg/tablet |
|---|---|---|
| Composition A |  |  |
| (a) Active ingredient | 250 | 250 |
| (b) Lactose B.P. | 210 | 26 |
| (c) Sodium Starch Glycollate | 20 | 12 |
| (d) Povidone B.P. | 15 | 9 |
| (e) Magnesium Stearate | 5 | 3 |
|  | 500 | 300 |
| Composition B |  |  |
| (a) Active ingredient | 250 | 250 |
| (b) Lactose 150 | 150 | — |
| (c) Avicel PH 101 | 60 | 26 |
| (d) Sodium Starch Glycollate | 20 | 12 |
| (e) Povidone B.P. | 15 | 9 |
| (f) Magnesium Stearate | 5 | 3 |
|  | 500 | 300 |
| Composition C |  |  |
| Active ingredient | 100 |  |
| Lactose | 200 |  |
| Starch | 50 |  |
| Povidone | 5 |  |
| Magnesium Stearate | 4 |  |
|  | 359 |  |

The following compositions D and E can be prepared by direct compression of the admixed ingredients. The lactose used in formulation E is of the direct compression type.

|  | mg/tablet |
|---|---|
| Composition D |  |
| Active ingredient | 250 |
| Magnesium Stearate | 4 |
| Pregelatinised Starch NF15 | 146 |
|  | 400 |
| Composition E |  |
| Active ingredient | 250 |
| Magnesium Stearate | 5 |
| Lactose | 145 |
| Avicel | 100 |
|  | 500 |
| Composition F (Controlled release composition) |  |
| (a) Active ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
|  | 700 |

The composition can be prepared by wet granulation of ingredients (a) to (c) with a solution of povidone, followed by addition of the magnesium stearate and compression.

Composition G (Enteric-Coated Tablet)

Enteric-coated tablets of Composition C can be prepared by coating the tablets with 25 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-Coated Controlled Release Tablet)

Enteric-coated tablets of Composition F can be prepared by coating the tablets with 50 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudgragit L). Except for Eudgragit L, these polymers should also include 10% (by weight of the quantity of polymer used) of a plasticizer to prevent membrane cracking during application or on storage. Suitable plasticizers include diethyl phthalate, tributyl citrate and triacetin.

(ii) Capsule Compositions

Composition A

Capsules can be prepared by admixing the ingredients of Composition D above and filling two-part hard gelatin capsules with the resulting mixture. Composition B (infra) may be prepared in a similar manner.

|  | mg/capsule |
|---|---|
| Composition B | |
| (a) Active ingredient | 250 |
| (b) Lactose B.P. | 143 |
| (c) Sodium Starch Glycollate | 25 |
| (d) Magnesium Stearate | 2 |
|  | 420 |
| Composition C | |
| (a) Active ingredient | 250 |
| (b) Macrogol 4000 BP | 350 |
|  | 600 |

Capsules can be prepared by melting the Macrogol 4000 BP, dispersing the active ingredient in the melt and filling two-part hard gelatin capsules therewith.

| Composition D | |
|---|---|
|  | mg/capsule |
| Active ingredient | 250 |
| Lecithin | 100 |
| Arachis Oil | 100 |
|  | 450 |

Capsules can be prepared by dispersing the active ingredient in the lecithin and arachis oil and filling soft, elastic gelatin capsules with the dispersion.

| Composition E (Controlled release capsule) | |
|---|---|
|  | mg/capsule |
| (a) Active ingredient | 250 |
| (b) Microcrystalline Cellulose | 125 |
| (c) Lactose BP | 125 |
| (d) Ethyl Cellulose | 13 |
|  | 513 |

The controlled release capsule formulation can be prepared by extruding mixed ingredients (a) to (c) using an extruder, then spheronising and drying the extrudate. The dried pellets are coated with a release controlling membrane (d) and filled into two-part, hard gelatin capsules.

| Composition F (Enteric capsule) | |
|---|---|
|  | mg/capsule |
| (a) Active ingredient | 250 |
| (b) Microcrystalline Cellulose | 125 |
| (c) Lactose BP | 125 |
| (d) Cellulose Acetate Phthalate | 50 |
| (e) Diethyl Phthalat | 5 |
|  | 555 |

The enteric capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-Coated Controlled Release Capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudragit L). Except for Eudragit L, these polymers should also include 10% (by weight of the quantity of polymer used) or a plasticizer to prevent membrane cracking during application or on storage. Suitable plasticizers include diethyl phthalate, tributyl citrate and triacetin.

| (iii) Intravenous injection composition | |
|---|---|
| Active ingredient | 0.200 g |
| Sterile, pyrogen-free phosphate buffer (pH 9.0) to | 10 ml |

The active ingredient is dissolved in most of the phosphate buffer at 35-40° C., then made up to volume and filtered through a sterile micropore filter into sterile 10 ml glass vials (Type 1) which are sealed with sterile closures and overseals.

| (iv) Intramuscular injection composition | |
|---|---|
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

| (v) Syrup composition | |
|---|---|
| Active ingredient | 0.25 g |
| Sorbitol Solution | 1.50 g |
| Glycerol | 1.00 g |
| Sodium Benzoate | 0.005 g |

| (v) Syrup composition | | |
|---|---|---|
| Flavour | | 0.0125 ml |
| Purified Water | q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

| (vi) Suppository composition | |
|---|---|
| | mg/suppository |
| Active ingredient | 250 |
| Hard Fat, BP (Witepsol H15 - Dynamit NoBel) | 1770 |
| | 2020 |

One-fifth of the Witepsol H15 is melted in a steam-jacketed pan at 45° C. maximum. The active ingredient is sifted through a 200 lm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 lm stainless steel screen and, with continuous stirring, allowed to cool to 40° C. At a temperature of 38-40° C., 2.02 g aliquots of the mixture are filled into suitable plastic moulds and the suppositories allowed to cool to room temperature.

| (vii) Pessary composition | |
|---|---|
| | mg/pessary |
| Active ingredient (63 lm) | 250 |
| Anhydrous Dextrose | 380 |
| Potato Starch | 363 |
| Magnesium Stearate | 7 |
| | 1000 |

The above ingredients are mixed directly and pessaries prepared by compression of the resulting mixture.

| (viii) Transdermal composition | |
|---|---|
| Active ingredient | 200 mg |
| Alcohol USP | 0.1 ml |
| Hydroxyethyl cellulose | |

The active ingredient and alcohol USP are gelled with hydroxyethyl cellulose and packed in a transdermal device with a surface area of 10 cm$^2$.

Compounds of the present invention show biological activity in the assay described hereinbefore, as illustrated by the following table:

| Example No. | IC$_{50}$ (nM) |
|---|---|
| 2 | 119 |
| 4 | 72 |
| 7 | 210 |
| 8 | 5 |
| 10 | 11 |
| 11 | 15 |
| 12 | 7 |
| 14 | 9 |

The invention claimed is:

1. A compound of formula (Ib):

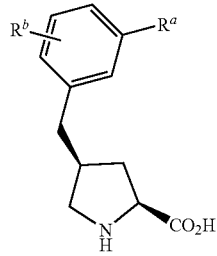

(Ib)

wherein $R^a$ is selected from halogen, hydroxy, cyano, nitro, amino, hydroxycarbonyl, $C_1$-$C_6$ alkyl, $C_1$-$C_6$ alkenyl, $C_1$-$C_6$ alkynyl, hydroxy$C_1$-$C_6$ alkyl, $C_1$-$C_6$ alkoxy$C_1$-$C_6$ alkyl, perfluoro$C_1$-$C_6$ alkoxy, $C_1$-$C_6$ alkylamino, di-$C_1$-$C_6$ alkylamino, amino$C_1$-$C_6$ alkyl, $C_1$-$C_6$ alkylamino$C_1$-$C_6$ alkyl, di-$C_1$-$C_6$ alkylamino$C_1$-$C_6$ alkyl, and $C_1C_6$ alkylthio; $R^b$ is selected from hydrogen, halogen, hydroxy, $(C_1$-$C_6)$alkoxy cyano, nitro, amino, hydroxycarbonyl, $C_1$-$C_6$ alkyl, $C_1$-$C_6$ alkenyl, $C_1$-$C_6$ alkynyl, $C_1$-$C_6$ alkoxy, hydroxy$C_1$-$C_6$ alkyl, $C_1C_6$ alkoxy$C_1$-$C_6$ alkyl, perfluoro $C_1$-$C_6$alkyl, perfluoro$C_1$-$C_6$ alkoxy, $C_1$-$C_6$ alkylamino, di-$C_1C_6$ alkylamino, amino$C_1$-$C_6$ alkyl, $C_1$-$C_6$ alkylamino$C_1$-$C_6$ alkyl, di-$C_1$-$C_6$ alkylamino$C_1$-$C_6$ alkyl, and $C_1$-$C_6$alkylthio; or a pharmaceutically acceptable salt thereof.

2. A compound of formula (1b) according to claim 1 which is selected from the group consisting of:

(2S,4S)-4-(2,3-Difluoro-benzyl)-pyrrolidine-2-carboxylic acid; and (2S,4S)-4-(2,5-Difluoro-benzyl)-pyrrolidine-2-carboxylic acid; or a pharmaceutically acceptable salt thereof.

3. A pharmaceutical composition comprising a compound of formula (1b) according to claim 1, or a pharmaceutically acceptable salt thereof, and one or more pharmaceutically acceptable excipients, diluents or carriers.

4. A pharmaceutical composition comprising a compound of formula (1b) according to claim 1, or a pharmaceutically acceptable salt thereof, and at least one other therapeutically active agent.

5. A pharmaceutical composition according to claim 4, wherein the other therapeutically active agent is a PDEV inhibitor selected from sildenafil, vardenafil, tadalafil, 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine, 5-(5-acetyl-2-butoxy-3-pyridinyl)-3-ethyl-2-(1-ethyl-3-azetidinyl)-2,6-dihydro-7H-pyrazolo[4,3-d] pyrimidin-7-one and 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one.

6. The compound (2S,4S)-4-(3-Fluoro-benzyl)-pyrrolidine-2-carboxylic acid, or a pharmaceutically acceptable salt thereof.

7. The compound (2S,4S)-4-(2,3-difluoro-benzyl)-pyrrolidine-2-carboxylic acid or a pharmaceutically acceptable salt thereof.

8. The compound (2S,4S)-4-(2,5-Difluoro-benzyl)-pyrrolidine-2-carboxylic acid, or a pharmaceutically acceptable salt thereof.

9. The compound, (2S,4S)-4-(3-fluoro-benzyl)-pyrrolidine-2-carboxylic acid mono hydrochloride salt.

* * * * *

UNITED STATES PATENT AND TRADEMARK OFFICE
CERTIFICATE OF CORRECTION

| | | |
|---|---|---|
| PATENT NO. | : 7,659,305 B2 | Page 1 of 1 |
| APPLICATION NO. | : 10/698354 | |
| DATED | : February 9, 2010 | |
| INVENTOR(S) | : David James Rawson | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1384 days.

Signed and Sealed this

Thirtieth Day of November, 2010

David J. Kappos
*Director of the United States Patent and Trademark Office*